US012629107B2

(12) United States Patent
Hiasa

(10) Patent No.: US 12,629,107 B2
(45) Date of Patent: May 19, 2026

(54) LEARNING METHOD, IMAGE PROCESSING METHOD, LEARNING APPARATUS, IMAGE PROCESSING APPARATUS, LEARNING PROGRAM, AND IMAGE PROCESSING PROGRAM

(71) Applicant: FUJIFILM Corporation, Tokyo (JP)

(72) Inventor: Yuta Hiasa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 261 days.

(21) Appl. No.: 18/395,717

(22) Filed: Dec. 25, 2023

(65) Prior Publication Data

US 2024/0122556 A1 Apr. 18, 2024

Related U.S. Application Data

(63) Continuation of application No. PCT/JP2022/024495, filed on Jun. 20, 2022.

(30) Foreign Application Priority Data

Jun. 29, 2021 (JP) ................................. 2021-107711

(51) Int. Cl.
*A61B 6/03* (2006.01)
*A61B 6/00* (2006.01)
(Continued)

(52) U.S. Cl.
CPC ............ *A61B 6/032* (2013.01); *A61B 6/5217* (2013.01); *G06T 7/0016* (2013.01); *G16H 30/40* (2018.01);
(Continued)

(58) Field of Classification Search
CPC ....... A61B 6/032; A61B 6/5217; A61B 6/482; A61B 6/5223; A61B 6/5235;
(Continued)

(56) References Cited

U.S. PATENT DOCUMENTS

2018/0061058 A1    3/2018    Xu et al.
2018/0182102 A1*   6/2018    Jerebko ..................... G06T 7/11
(Continued)

FOREIGN PATENT DOCUMENTS

EP       3667609       6/2020
JP       2019526863    9/2019
(Continued)

OTHER PUBLICATIONS

Task Driven Generative Modeling for Unsupervised Domain Adaptation: Application to X-ray Image Segmentation (Year: 2018).*
(Continued)

*Primary Examiner* — Jennifer Mehmood
*Assistant Examiner* — Pardis Sohraby
(74) *Attorney, Agent, or Firm* — JCIPRNET

(57) ABSTRACT

An embodiment of the present invention provides a learning method, a learning apparatus, and a learning program for decomposing a two-dimensional X-ray image into a variety of regions, and an image processing method, an image processing apparatus, and an image processing program using a result of learning. A learning method according to an aspect of the present invention includes generating a masked CT image from a three-dimensional CT image, and generating a third pseudo X-ray image from the masked CT image. Then, a second pseudo X-ray image generated by projecting an original CT image is compared with the third pseudo X-ray image as a reference, and a parameter for use in generating the second pseudo X-ray image is updated based on a comparison result. A processor repeats the processing of each step until a predetermined condition is satisfied.

17 Claims, 14 Drawing Sheets

(51) Int. Cl.
  *G06T 7/00*          (2017.01)
  *G16H 30/40*         (2018.01)

(52) U.S. Cl.
  CPC .............. *G06T 2207/10116* (2013.01); *G06T 2207/20081* (2013.01)

(58) Field of Classification Search
  CPC ......... G06T 7/0016; G06T 2207/10116; G06T 2207/20081; G06T 11/008; G16H 30/40
  USPC ......................................................... 382/132
  See application file for complete search history.

(56)                    References Cited

U.S. PATENT DOCUMENTS

| | | | | |
|---|---|---|---|---|
| 2020/0184639 A1* | 6/2020 | Park | .................. | G06T 11/003 |
| 2020/0321101 A1 | 10/2020 | Karargyris et al. | | |
| 2020/0380313 A1 | 12/2020 | Keshwani et al. | | |
| 2020/0380680 A1 | 12/2020 | Aoyagi et al. | | |
| 2021/0365717 A1 | 11/2021 | Cao et al. | | |
| 2023/0015933 A1 | 1/2023 | Aoyagi et al. | | |
| 2024/0164733 A1* | 5/2024 | Florent | .................. | G06T 7/00 |

FOREIGN PATENT DOCUMENTS

| | | |
|---|---|---|
| JP | 2019165923 | 10/2019 |
| JP | 2020093083 | 6/2020 |
| JP | 2020192006 | 12/2020 |
| WO | 2019167883 | 9/2019 |
| WO | 2020215985 | 10/2020 |

OTHER PUBLICATIONS

"Office Action of Europe Counterpart Application", issued on Jul. 11, 2025, pp. 1-5.

Wei Yang et al., "Cascade of multi-scale convolutional neural networks for bone suppression of chest radiographs in gradient domain", Medical Image Analysis, Aug. 16, 2016, pp. 1-14.

Han Li et al., "High-Resolution Chest X-Ray Bone Suppression Using Unpaired CT Structural Priors", IEEE Transactions on Medical Imaging, Apr. 7, 2020, pp. 3053-3063.

"International Search Report (Form PCT/ISA/210) of PCT/JP2022/024495," mailed on Jul. 26, 2022, with English translation thereof, pp. 1-8.

"Written Opinion of the International Searching Authority (Form PCT/ISA/237) of PCT/JP2022/024495," mailed on Jul. 26, 2022, with English translation thereof, pp. 1-8.

Yue Zhang et al., "Task Driven Generative Modeling for Unsupervised Domain Adaptation: Application to X-ray Image Segmentation", Medical Image Computing and Computer Assisted Intervention—MICCAI 2018, Sep. 26, 2018, pp. 599-607.

"Search Report of Europe Counterpart Application", issued on Oct. 2, 2024, pp. 1-9.

"Notice of Reasons for Refusal of Japan Counterpart Application", issued on Jan. 5, 2026, with English translation thereof, p. 1-p. 11.

* cited by examiner

Figure 3:
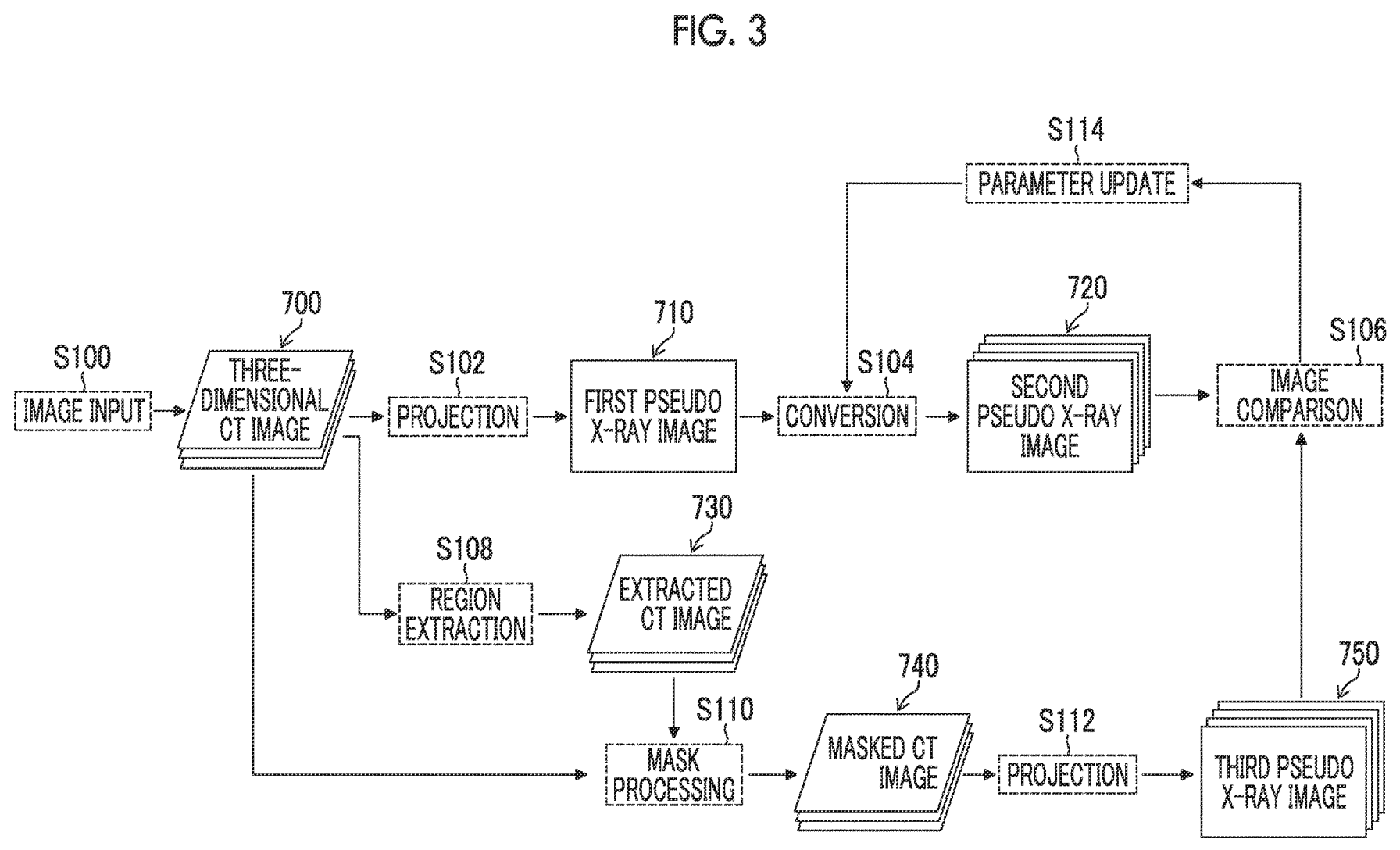

S100 — IMAGE INPUT

700 — THREE-DIMENSIONAL CT IMAGE

S102 — PROJECTION

710 — FIRST PSEUDO X-RAY IMAGE

S104 — CONVERSION

720 — SECOND PSEUDO X-RAY IMAGE

S106 — IMAGE COMPARISON

S114 — PARAMETER UPDATE

S108 — REGION EXTRACTION

730 — EXTRACTED CT IMAGE

S110 — MASK PROCESSING

740 — MASKED CT IMAGE

S112 — PROJECTION

750 — THIRD PSEUDO X-RAY IMAGE

Figure 9:
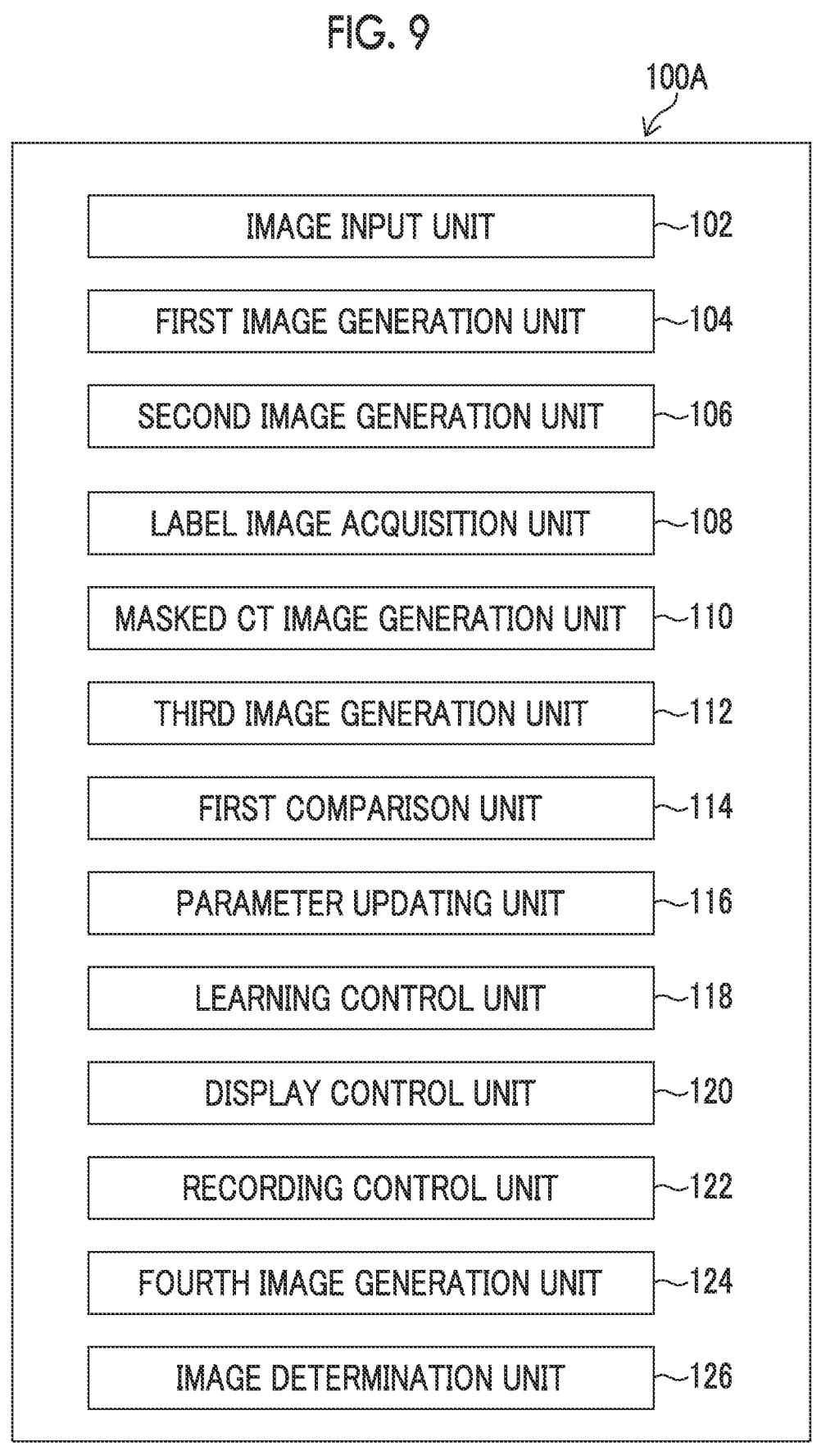

| IMAGE INPUT UNIT | ~102 |
| FIRST IMAGE GENERATION UNIT | ~104 |
| SECOND IMAGE GENERATION UNIT | ~106 |
| LABEL IMAGE ACQUISITION UNIT | ~108 |
| MASKED CT IMAGE GENERATION UNIT | ~110 |
| THIRD IMAGE GENERATION UNIT | ~112 |
| FIRST COMPARISON UNIT | ~114 |
| PARAMETER UPDATING UNIT | ~116 |
| LEARNING CONTROL UNIT | ~118 |
| DISPLAY CONTROL UNIT | ~120 |
| RECORDING CONTROL UNIT | ~122 |
| FOURTH IMAGE GENERATION UNIT | ~124 |
| IMAGE DETERMINATION UNIT | ~126 |

Figure 13:
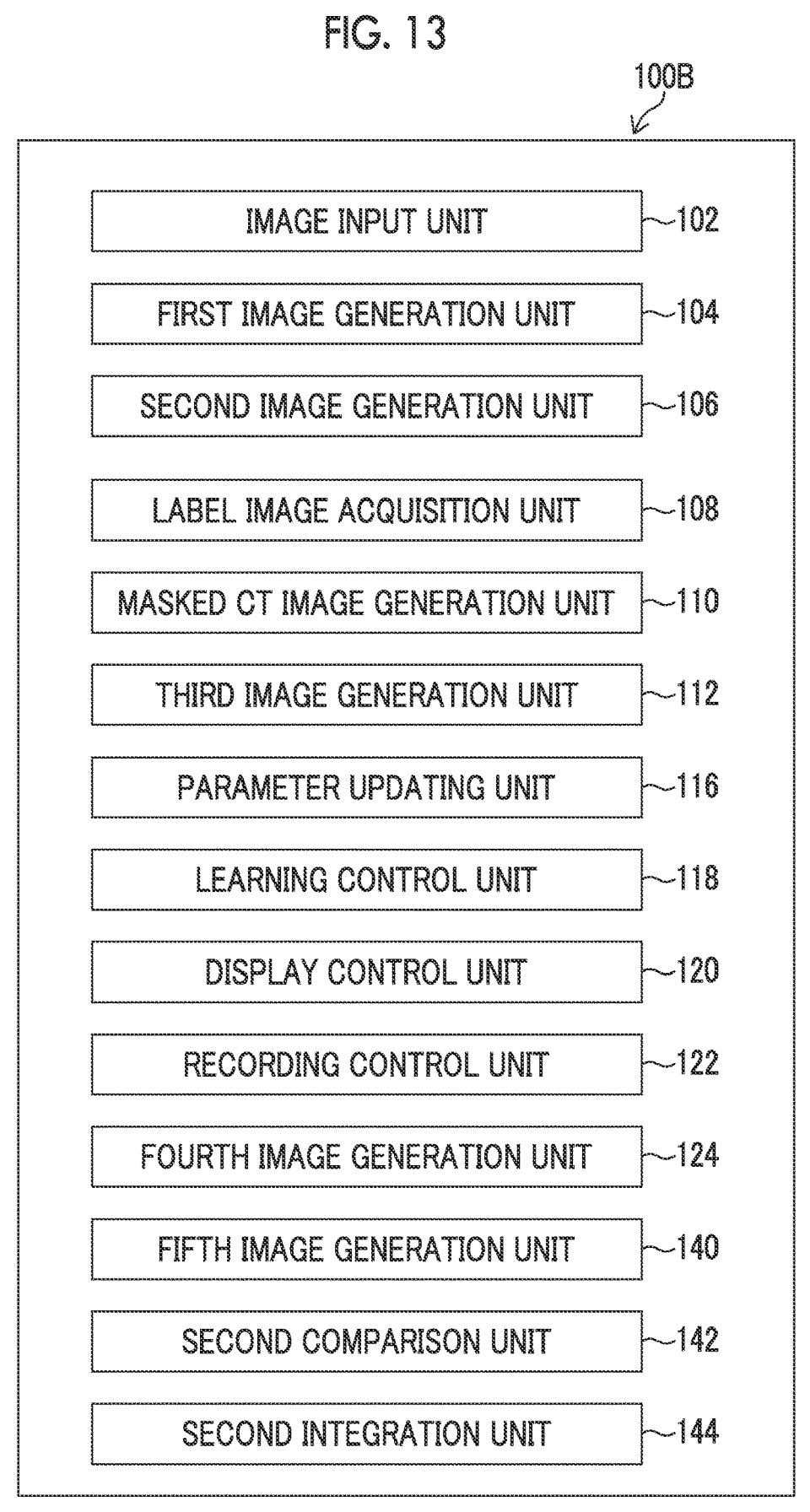

| | |
|---|---|
| IMAGE INPUT UNIT | ~102 |
| FIRST IMAGE GENERATION UNIT | ~104 |
| SECOND IMAGE GENERATION UNIT | ~106 |
| LABEL IMAGE ACQUISITION UNIT | ~108 |
| MASKED CT IMAGE GENERATION UNIT | ~110 |
| THIRD IMAGE GENERATION UNIT | ~112 |
| PARAMETER UPDATING UNIT | ~116 |
| LEARNING CONTROL UNIT | ~118 |
| DISPLAY CONTROL UNIT | ~120 |
| RECORDING CONTROL UNIT | ~122 |
| FOURTH IMAGE GENERATION UNIT | ~124 |
| FIFTH IMAGE GENERATION UNIT | ~140 |
| SECOND COMPARISON UNIT | ~142 |
| SECOND INTEGRATION UNIT | ~144 |

| SIMPLE X-RAY IMAGE | → | CONVERSION | → | DECOMPOSED IMAGE (SECOND PSEUDO X-RAY IMAGE) |

1

LEARNING METHOD, IMAGE PROCESSING METHOD, LEARNING APPARATUS, IMAGE PROCESSING APPARATUS, LEARNING PROGRAM, AND IMAGE PROCESSING PROGRAM

CROSS-REFERENCE TO RELATED APPLICATIONS

The present application is a Continuation of PCT International Application No. PCT/JP2022/024495 filed on Jun. 20, 2022 claiming priority under 35 U.S.C. § 119(a) to Japanese Patent Application No. 2021-107711 filed on Jun. 29, 2021. Each of the above applications is hereby expressly incorporated by reference, in its entirety, into the present application.

BACKGROUND OF THE INVENTION

1. Field of the Invention

The present invention relates to learning of a medical-use image and medical-use image processing.

2. Description of the Related Art

In a field of handling a medical-use image (may also be referred to as a medical image), such as an X-ray image or a computed tomography (CT) image, decomposition of a captured image into a plurality of anatomical regions is performed. In a case where such image decomposition is performed, because a bone is projected in a simple X-ray image in a superimposed manner in addition to an organ or a blood vessel, an anatomical structure or a disease is not easily recognized. In contrast, while a bone and a soft tissue can be decomposed by imaging using an X-ray source with a plurality of energy bands, dedicated imaging equipment is required.

In such a field, a decomposition method of a simple X-ray image by machine learning has been developed. For example, "Cascade of multi-scale convolutional neural networks for bone suppression of chest radiographs in gradient domain", Medical image analysis, 2017, Yang, Wei, et al., [Searched on Jun. 14, 2021], Internet (https://www.researchgate.net/publication/306111633_Cascade_of multi-scale_convolutional_neural_networks_for_bone_suppression_of_chest_radiographs_in_gradient_domain) and "High-resolution chest X-ray bone suppression using unpaired CT structural priors.", IEEE transactions on medical imaging, 2020, Li, Han, et al., [Searched on Jun. 14, 2021], Internet (https://vipl.ict.ac.cn/uploadfile/upload/2021020215302777.pdf) describe that a simple X-ray image is decomposed into a bone and a soft tissue using a convolutional neural network (CNN).

SUMMARY OF THE INVENTION

An embodiment according to the technique of the present disclosure provides a learning method, a learning apparatus, and a learning program for decomposing a two-dimensional X-ray image into a variety of regions, and an image processing method, an image processing apparatus, and an image processing program using a result of learning.

To attain the above-described object, there is provided a learning method according to a first aspect of the present invention comprising inputting a three-dimensional CT image of a subject, projecting the three-dimensional CT image into a two-dimensional space to generate a first pseudo X-ray image, generating, from the first pseudo X-ray image, a second pseudo X-ray image that is a plurality of images in which a plurality of anatomical regions of the subject are respectively decomposed and shown, acquiring a label image in which the plurality of anatomical regions are labeled to the three-dimensional CT image, generating a masked CT image that is a three-dimensional image in which the plurality of anatomical regions are respectively decomposed and shown, based on the three-dimensional CT image and the label image, projecting the masked CT image into a two-dimensional space to generate a third pseudo X-ray image that is a plurality of images in which the plurality of anatomical regions are respectively decomposed and shown, comparing the second pseudo X-ray image and the third pseudo X-ray image, updating a value of a parameter for use in generating the second pseudo X-ray image based on a result of the comparison, and repeating the input of the three-dimensional CT image, the generation of the first pseudo X-ray image, the generation of the second pseudo X-ray image, the acquisition of the label image, the generation of the masked CT image, the generation of the third pseudo X-ray image, the comparison of the second pseudo X-ray image and the third pseudo X-ray image, and the update of the value of the parameter until a predetermined condition is satisfied.

According to a second aspect, in the learning method of the first aspect, in the comparison of the second pseudo X-ray image and the third pseudo X-ray image, an error of the second pseudo X-ray image with respect to the third pseudo X-ray image as a reference is calculated, and in the update of the value of the parameter, the error is reduced by updating the parameter.

According to a third aspect, in the learning method of the first aspect, in the comparison of the second pseudo X-ray image and the third pseudo X-ray image, an error of the second pseudo X-ray image with respect to the third pseudo X-ray image as a reference is calculated, the third pseudo X-ray image and the second pseudo X-ray image are discriminated, and the error and a result of the discrimination are integrated, and in the update of the value of the parameter, a result of the integration is reduced by updating the parameter.

According to a fourth aspect, in the learning method of the first aspect, in the comparison of the second pseudo X-ray image and the third pseudo X-ray image, an error of the second pseudo X-ray image with respect to the third pseudo X-ray image as a reference is calculated, pair data of the first pseudo X-ray image and the third pseudo X-ray image and pair data of the first pseudo X-ray image and the second pseudo X-ray image are discriminated, and the error and a result of the discrimination are integrated, and in the update of the value of the parameter, a result of the integration is reduced by updating the parameter.

According to a fifth aspect, in the learning method of any one of the first to fourth aspects, in the acquisition of the label image, the label image is acquired by generating the label image from the three-dimensional CT image.

According to a sixth aspect, in the learning method of any one of the first to fifth aspects, in the generation of the masked CT image, a mask image is generated from an extracted CT image obtained by performing region extraction on the three-dimensional CT image, and the extracted CT image is multiplied by the mask image to generate the masked CT image.

According to a seventh aspect, in the learning method of any one of the first to sixth aspects, a simple X-ray image is further input in the input of the three-dimensional CT image, a fourth pseudo X-ray image that is a plurality of images in which the plurality of anatomical regions are respectively decomposed and shown is generated from the simple X-ray image, the second pseudo X-ray image and the fourth pseudo X-ray image are discriminated, and in the update of the value of the parameter, the value of the parameter is updated further based on a result of the discrimination of the second pseudo X-ray image and the fourth pseudo X-ray image.

According to an eighth aspect, in the learning method of the seventh aspect, the fourth pseudo X-ray image is converted into a first segmentation label, a second segmentation label for the simple X-ray image is acquired, the first segmentation label and the second segmentation label are compared, the result of the comparison of the second pseudo X-ray image and the third pseudo X-ray image and a result of the comparison of the first segmentation label and the second segmentation label are integrated, and in the update of the value of the parameter, the parameter is updated based on the integrated result of the comparison.

According to a ninth aspect, in the learning method of any one of the first to sixth aspects, in the input of the three-dimensional CT image, a simple X-ray image and a dual energy X-ray image that is a plurality of X-ray images which are captured with X-rays of different energy levels and in which different anatomical regions of the subject are high-lighted are input, a fourth pseudo X-ray image that is a plurality of images in which the plurality of anatomical regions are respectively decomposed and shown is generated from the simple X-ray image, the fourth pseudo X-ray image is reconstructed to generate a fifth pseudo X-ray image that is a plurality of images in which the same anatomical regions as X-ray images composing the dual energy X-ray image are respectively highlighted, the dual energy X-ray image and the fifth pseudo X-ray image are compared, a result of the comparison of the dual energy X-ray image and the fifth pseudo X-ray image is integrated with the result of the comparison of the second pseudo X-ray image and the third pseudo X-ray image, and in the update of the value of the parameter, the parameter is updated based on the integrated result of the comparison.

To attain the above-described object, there is provided an image processing method according to a tenth aspect of the present invention comprising acquiring a simple X-ray image or a pseudo X-ray image, and converting the acquired simple X-ray image or pseudo X-ray image with a parameter updated by the learning method according to any one of the first to ninth aspects to generate a decomposed image that is a plurality of images in which a plurality of anatomical regions of the subject are respectively decomposed and shown.

According to an eleventh aspect, in the image processing method of the tenth aspect, the decomposed image is converted into a segmentation label.

To attain the above-described object, there is provided a learning apparatus according to a twelfth aspect of the present invention comprising a processor, in which the processor is configured to input a three-dimensional CT image of a subject, project the three-dimensional CT image into a two-dimensional space to generate a first pseudo X-ray image, generate, from the first pseudo X-ray image, a second pseudo X-ray image that is a plurality of images in which a plurality of anatomical regions of the subject are respectively decomposed and shown, acquire a label image in which the plurality of anatomical regions are labeled to the three-dimensional CT image, generate a masked CT image that is a three-dimensional image in which the plurality of anatomical regions are respectively decomposed and shown, based on the three-dimensional CT image and the label image, project the masked CT image into a two-dimensional space to generate a third pseudo X-ray image that is a plurality of images in which the plurality of anatomical regions are respectively decomposed and shown, compare the second pseudo X-ray image and the third pseudo X-ray image, update a value of a parameter for use in generating the second pseudo X-ray image based on a result of the comparison, and repeat the input of the three-dimensional CT image, the generation of the first pseudo X-ray image, the generation of the second pseudo X-ray image, the acquisition of the label image, the generation of the masked CT image, the generation of the third pseudo X-ray image, the comparison of the second pseudo X-ray image and the third pseudo X-ray image, and the update of the value of the parameter until a predetermined condition is satisfied.

To attain the above-described object, there is provided an image processing apparatus according to a thirteenth aspect of the present invention comprising a processor, in which the processor is configured to acquire a simple X-ray image or a pseudo X-ray image, and convert the acquired simple X-ray image or pseudo X-ray image with a parameter updated by the learning method according to any one of the first to ninth aspects to generate a decomposed image that is a plurality of images in which a plurality of anatomical regions of the subject are respectively decomposed and shown.

According to a fourteenth aspect, in the image processing apparatus of the thirteenth aspect, the processor is configured to convert the decomposed image into a segmentation label.

To attain the above-described object, there is provided a learning program according to a fifteenth aspect of the present invention that causes a learning apparatus including a processor to execute a learning method, the learning method comprising inputting a three-dimensional CT image of a subject, projecting the three-dimensional CT image into a two-dimensional space to generate a first pseudo X-ray image, generating, from the first pseudo X-ray image, a second pseudo X-ray image that is a plurality of images in which a plurality of anatomical regions of the subject are respectively decomposed and shown, acquiring a label image in which the plurality of anatomical regions are labeled to the three-dimensional CT image, generating a masked CT image that is a three-dimensional image in which the plurality of anatomical regions are respectively decomposed and shown, based on the three-dimensional CT image and the label image, projecting the masked CT image into a two-dimensional space to generate a third pseudo X-ray image that is a plurality of images in which the plurality of anatomical regions are respectively decomposed and shown, comparing the second pseudo X-ray image and the third pseudo X-ray image, updating a value of a parameter for use in generating the second pseudo X-ray image based on a result of the comparison, and causing the processor to repeat the input of the three-dimensional CT image, the generation of the first pseudo X-ray image, the generation of the second pseudo X-ray image, the acquisition of the label image, the generation of the masked CT image, the generation of the third pseudo X-ray image, the comparison of the second pseudo X-ray image and the third pseudo X-ray image, and the update of the value of the parameter until a predetermined condition is satisfied.

To attain the above-described object, there is provided an image processing program according to a sixteenth aspect of the present invention that causes an image processing apparatus including a processor to execute an image processing method, the image processing method comprising acquiring a simple X-ray image or a pseudo X-ray image, and converting the acquired simple X-ray image or pseudo X-ray image with a parameter updated by the learning method according to any one of the first to ninth aspects to generate a decomposed image that is a plurality of images in which a plurality of anatomical regions of the subject are respectively decomposed and shown.

According to a seventeenth aspect, the image processing program of the sixteenth aspect causes the processor to further execute converting the decomposed image into a segmentation label.

BRIEF DESCRIPTION OF THE DRAWINGS

FIG. 3 is a diagram showing a manner of learning in the first embodiment.

FIG. 9 is a diagram showing a functional configuration of a processor in a second embodiment.

FIG. 10 is a diagram showing a manner of learning in the second embodiment.

FIG. 13 is a diagram showing a functional configuration of a processor in a third embodiment.

FIG. 14 is a diagram showing a manner of learning in the third embodiment.

DESCRIPTION OF THE PREFERRED EMBODIMENTS

Figure 1:
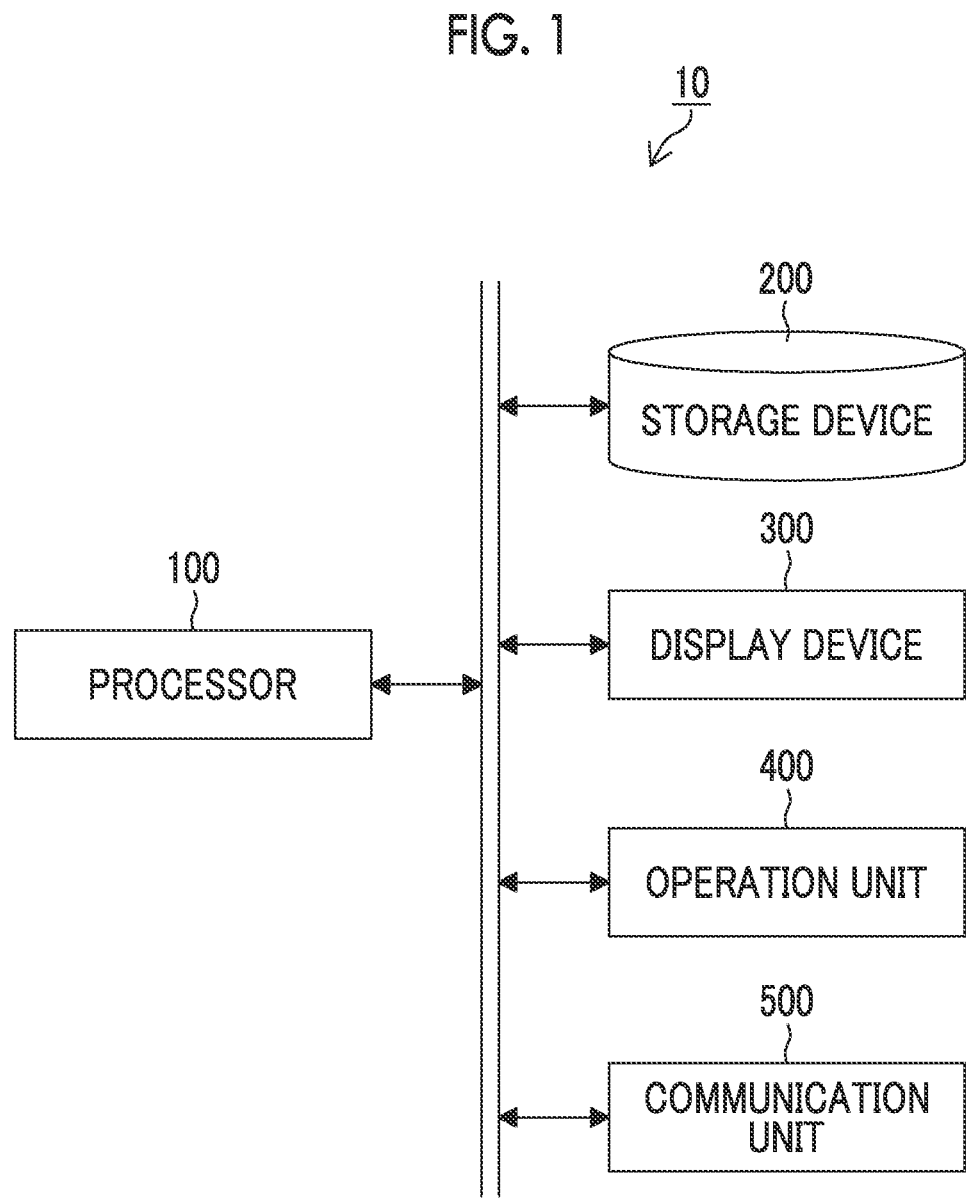
FIG. 1 is a diagram showing a schematic configuration of a learning apparatus according to a first embodiment.

An embodiment of a learning method, an image processing method, a learning apparatus, an image processing apparatus, a learning program, and an image processing program according to an aspect of the present invention will be described. In the description, the accompanying drawings will be referred to as necessary. In the accompanying drawings, some components may be omitted for convenience of description.

A learning method according to a first aspect of the present invention comprises an image input step of inputting a three-dimensional CT image of a subject, a first image generation step of projecting the three-dimensional CT image into a two-dimensional space to generate a first pseudo X-ray image, a second image generation step of generating, from the first pseudo X-ray image, a second pseudo X-ray image that is a plurality of images in which a plurality of anatomical regions of the subject are respectively decomposed and shown, a label image acquisition step of acquiring a label image in which the plurality of anatomical regions are labeled to the three-dimensional CT image, a masked CT image generation step of generating a masked CT image that is a three-dimensional image in which the plurality of anatomical regions are respectively decomposed and shown, based on the three-dimensional CT image and the label image, a third image generation step of projecting the masked CT image into a two-dimensional space to generate a third pseudo X-ray image that is a plurality of images in which the plurality of anatomical regions are respectively decomposed and shown, a first comparison step of comparing the second pseudo X-ray image and the third pseudo X-ray image, and an updating step of updating a value of a parameter for use in generating the second pseudo X-ray image based on a result of the comparison in the first comparison step, and causes a processor to repeat the image input step, the first image generation step, the second image generation step, the label image acquisition step, the masked CT image generation step, the third image generation step, the first comparison step, and the updating step until a predetermined condition is satisfied.

In the first aspect, the masked CT image is generated from the three-dimensional CT image, and the third pseudo X-ray image is generated from the masked CT image. Then, the second pseudo X-ray image generated by projecting an original CT image is compared with the third pseudo X-ray image as a reference, and the parameter is updated based on the comparison result.

In the first aspect, the processor repeats the processing of each step, and learning (parameter update) progresses. The order of the processing at the time of the repetition may not always be the described order. For example, various methods, such as serial processing, batch processing, and mini batch processing, can be used. In the first aspect, as the "predetermined condition" for ending the processing, various conditions, such as the number of times of update of the parameter, the comparison result satisfying a reference, and the end of the processing on all images, can be used.

In a case where learning ends in such a manner (in a case where the "predetermined condition" is satisfied and the update of the parameter ends), the two-dimensional X-ray image can be decomposed into a variety of regions using the above-described parameter.

In the first aspect and each aspect described below, a plurality of images in which a plurality of anatomical regions are respectively decomposed and shown may be referred to as a "decomposed image", and an image in which a plurality of anatomical regions are shown without being decomposed may be referred to as a "non-decomposed image". In the first aspect and each aspect described below, a method of machine learning, such as deep learning, may be used for processing, such as image generation, label acquisition, and image comparison.

According to a second aspect, in the learning method of the first aspect, in the first comparison step, an error of the second pseudo X-ray image with respect to the third pseudo X-ray image as a reference is calculated, and in the updating step, the error is reduced by updating the parameter. According to the second aspect, the error (the error of the second pseudo X-ray image with respect to the third pseudo X-ray image as a reference) is reduced by the update of the parameter, and the second pseudo X-ray image (decomposed image) can be generated with excellent accuracy.

According to a third aspect, the learning method of the first aspect further has, in the first comparison step, a step of calculating an error of the second pseudo X-ray image with respect to the third pseudo X-ray image as a reference, a discrimination step of discriminating the third pseudo X-ray image and the second pseudo X-ray image, and a step of integrating the error and a result of the discrimination, and in the updating step, a result of the integration is reduced by updating the parameter.

According to a fourth aspect, the learning method of the first aspect further has, in the first comparison step, a step of calculating an error of the second pseudo X-ray image with respect to the third pseudo X-ray image as a reference, a discrimination step of discriminating pair data of the first pseudo X-ray image and the third pseudo X-ray image and pair data of the first pseudo X-ray image and the second pseudo X-ray image, and a step of integrating the error and a result of the discrimination, and in the updating step, a result of the integration is reduced by updating the parameter.

According to a fifth aspect, in the learning method of any one of the first to fourth aspects, in the label image acquisition step, the label image is acquired by generating the label image from the three-dimensional CT image. The fifth aspect defines an aspect of a label image generation method.

According to a sixth aspect, in the learning method of any one of the first to fifth aspects, in the masked CT image generation step, a mask image is generated from an extracted CT image obtained by performing region extraction on the three-dimensional CT image, and the CT image is multiplied by the mask image to generate the masked CT image. The sixth aspect defines an aspect of a masked CT image generation method.

According to a seventh aspect, in the learning method of any one of the first to sixth aspects, a simple X-ray image is further input in the image input step, the learning method further has a fourth image generation step of generating, from the simple X-ray image, a fourth pseudo X-ray image that is a plurality of images in which a plurality of anatomical regions are respectively decomposed and shown, and a discrimination step of discriminating the second pseudo X-ray image and the fourth pseudo X-ray image, and in the updating step, the value of the parameter is updated further based on a result of the discrimination.

In the seventh aspect, an image captured in a posture different from in the CT image and the simple X-ray image may be employed. For example, while CT image is often captured in a supine posture, and the simple X-ray image is often captured in an upright posture, even in such a case, as in the seventh aspect, the pseudo X-ray image (fourth pseudo X-ray image) based on the simple X-ray image is reflected in the updated of the parameter, so that it is possible to reduce an influence of domain shifting.

In the seventh aspect, while it is preferable that the three-dimensional CT image and the simple X-ray image are images obtained by imaging the same subject, the seventh aspect can also be applied to a case where the images are images obtained by imaging different subjects.

According to an eighth aspect, the learning method of the seventh aspect causes the processor to further execute a first label acquisition step of acquiring a first segmentation label for the simple X-ray image, a second label acquisition step of converting the fourth pseudo X-ray image into a second segmentation label, a label comparison step of comparing the first segmentation label and the second segmentation label, and a first integration step of integrating a result of the comparison in the first comparison step and a result of the comparison in the label comparison step, and in the updating step, the parameter is updated based on the results of the comparison integrated in the first integration step. An integration method of the comparison results in the eighth aspect is not particularly limited, and for example, simple addition, weighted addition, and averaging can be performed.

According to a ninth aspect, in the learning method of any one of the first to sixth aspects, in the image input step, a simple X-ray image and a dual energy X-ray image that is a plurality of X-ray images which are captured with X-rays of different energy levels and in which different anatomical regions of the subject are highlighted are input, the learning method causes the processor to further execute a fourth image generation step of generating, from the simple X-ray image, a fourth pseudo X-ray image that is a plurality of images in which the plurality of anatomical regions are respectively decomposed and shown, a fifth image generation step of reconstructing the fourth pseudo X-ray image to generate a fifth pseudo X-ray image that is a plurality of images in which the same anatomical regions as X-ray images composing the dual energy X-ray image are respectively highlighted, a second comparison step of comparing the dual energy X-ray image and the fifth pseudo X-ray image, and a second integration step of integrating a result of the comparison in the second comparison step with a result of the comparison in the first comparison step, and in the updating step, the parameter is updated based on the integrated result of the comparison.

According to the ninth aspect, the dual energy X-ray image that is a plurality of X-ray images in which different anatomical regions (for example, bone and soft tissue) of the subject are highlighted with X-rays of different energy levels is input, and the dual energy X-ray image and the fifth pseudo X-ray image are compared (second comparison step). In this case, images captured in an upright posture can be used for both, and in this case, domain shifting due to the posture does not occur. Then, the comparison result in the second comparison step is integrated with the comparison result in the first comparison step, and the parameter is updated based on the integrated result of the comparison. According to the seventh aspect, the dual energy X-ray image and the pseudo X-ray image are complementarily combined in this way, so that it is possible to decompose the X-ray image into multiple regions while reducing domain shifting due to the posture. An integration method of the comparison results in the ninth aspect is not particularly limited, and for example, simple addition, weighted addition, and averaging can be performed.

To attain the above-described object, there is provided an image processing method according to a tenth aspect of the present invention that causes a processor to execute an image input step of acquiring a simple X-ray image or a pseudo X-ray image, and a decomposed image generation step of converting the acquired simple X-ray image or pseudo X-ray image with a parameter updated by the learning method according to any one of the first to ninth aspects to generate a decomposed image that is a plurality of images in which a plurality of anatomical regions of the subject are respectively decomposed and shown. In the tenth aspect, the decomposed image of a plurality of the anatomical regions can be acquired by converting the simple X-ray image or the pseudo X-ray image using the parameter updated by the learning method according to any one of the first to ninth aspects.

According to an eleventh aspect, the image processing method of the tenth aspect causes the processor to further execute a label acquisition step of converting the decomposed image into a segmentation label. The eleventh aspect is an aspect where the image processing method according to the tenth aspect is applied to segmentation.

To attain the above-described object, there is provided a learning apparatus according to a twelfth aspect of the present invention comprising a processor, in which the processor is configured to execute image input processing of inputting a three-dimensional CT image of a subject, first image generation processing of projecting the three-dimensional CT image into a two-dimensional space to generate a first pseudo X-ray image, second image generation processing of generating, from the first pseudo X-ray image, a second pseudo X-ray image that is a plurality of images in which a plurality of anatomical regions of the subject are respectively decomposed and shown, label image acquisition processing of acquiring a label image in which the plurality of anatomical regions are labeled to the three-dimensional CT image, masked CT image generation processing of generating a masked CT image that is a three-dimensional image in which the plurality of anatomical regions are respectively decomposed and shown, based on the three-dimensional CT image and the label image, third image generation processing of projecting the masked CT image into a two-dimensional space to generate a third pseudo X-ray image that is a plurality of images in which the plurality of anatomical regions are respectively decomposed and shown, first comparison processing of comparing the second pseudo X-ray image and the third pseudo X-ray image, updating processing of updating a value of a parameter for use in generating the second pseudo X-ray image based on a result of the comparison in the first comparison processing, and repeating processing of repeating the image input processing, the first image generation processing, the second image generation processing, the label image acquisition processing, the masked CT image generation processing, the third image generation processing, the first comparison processing, and the updating processing until a predetermined condition is satisfied.

According to the twelfth aspect, as in the first aspect, the two-dimensional X-ray image can be decomposed into a variety of regions. In the twelfth aspect, the processor may be configured to further execute the same processing as in the second to ninth aspects.

To attain the above-described object, there is provided an image processing apparatus according to a thirteenth aspect of the present invention comprising a processor, in which the processor is configured to execute image input processing of acquiring a simple X-ray image or a pseudo X-ray image, and decomposed image generation processing of converting the acquired simple X-ray image or pseudo X-ray image with a parameter updated by the learning method according to any one of the first to ninth aspects to generate a decomposed image that is a plurality of images in which a plurality of anatomical regions of the subject are respectively decomposed and shown. According to the thirteenth aspect, as in the tenth aspect, the decomposed image of a plurality of anatomical regions can be acquired.

According to a fourteenth aspect, in the image processing apparatus according to the thirteenth aspect, the processor is configured to further execute label acquisition processing of converting the decomposed image into a segmentation label. The fourteenth aspect is an aspect where the image processing apparatus according to the thirteenth aspect is applied to segmentation as in the eleventh aspect.

To attain the above-described object, there is provided a learning program according to a fifteenth aspect of the present invention that causes a learning apparatus including a processor to execute a learning method, the learning method comprising an image input step of inputting a three-dimensional CT image of a subject, a first image generation step of projecting the three-dimensional CT image into a two-dimensional space to generate a first pseudo X-ray image, a second image generation step of generating, from the first pseudo X-ray image, a second pseudo X-ray image that is a plurality of images in which a plurality of anatomical regions of the subject are respectively decomposed and shown, a label image acquisition step of acquiring a label image in which the plurality of anatomical regions are labeled to the three-dimensional CT image, a masked CT image generation step of generating a masked CT image that is a three-dimensional image in which the plurality of anatomical regions are respectively decomposed and shown, based on the three-dimensional CT image and the label image, a third image generation step of projecting the masked CT image into a two-dimensional space to generate a third pseudo X-ray image that is a plurality of images in which the plurality of anatomical regions are respectively decomposed and shown, a first comparison step of comparing the second pseudo X-ray image and the third pseudo X-ray image, and an updating step of updating a value of a parameter for use in generating the second pseudo X-ray image based on a result of the comparison in the first comparison step, and causes a processor to repeat the image input step, the first image generation step, the second image generation step, the label image acquisition step, the masked CT image generation step, the third image generation step, the first comparison step, and the updating step until a predetermined condition is satisfied.

According to the fifteenth aspect, as in the first and tenth aspects, the two-dimensional X-ray image can be decomposed into a variety of regions. The learning method that is executed by the learning program according to the present invention may have the same configuration as in the second to ninth aspects. A non-transitory recording medium storing a computer-readable code of the above-described learning program may be included in an aspect of the present invention.

To attain the above-described object, there is provided an image processing program according to a sixteenth aspect of the present invention that causes an image processing apparatus including a processor to execute an image processing method, the image processing method comprising an image input step of acquiring a simple X-ray image or a pseudo X-ray image, and a decomposed image generation step of converting the acquired simple X-ray image or pseudo X-ray image with a parameter updated by the learning method according to any one of the first to ninth aspects to generate a decomposed image that is a plurality of images in which a plurality of anatomical regions of the subject are respectively decomposed and shown.

According to the sixteenth aspect, as in the tenth and thirteenth aspects, the decomposed image of a plurality of anatomical regions can be acquired.

According to a seventeenth aspect, the image processing program of the sixteenth aspect causes the processor to further execute a label acquisition step of converting the decomposed image into a segmentation label. The seventeenth aspect is an aspect where the image processing apparatus according to the sixteenth aspect is applied to segmentation as in the eleventh and fourteenth aspects. The image processing method that is executed by the image processing program according to the present invention may have the same configuration as in the second to ninth aspects. A non-transitory recording medium storing a computer-readable code of the above-described learning program may be included in an aspect of the present invention.

First Embodiment

[Configuration of Learning Apparatus]

FIG. 1 is a diagram showing a schematic configuration of a learning apparatus 10 (learning apparatus, image processing apparatus) according to a first embodiment. The learning apparatus 10 comprises a processor 100 (processor), a storage device 200, a display device 300, an operation unit 400, and a communication unit 500. The connection between these components may be made in a wired or wireless manner. Further, these components may be stored in a single housing or may be separately stored in a plurality of housings.

[Functional Configuration of Processor]

Figure 2:
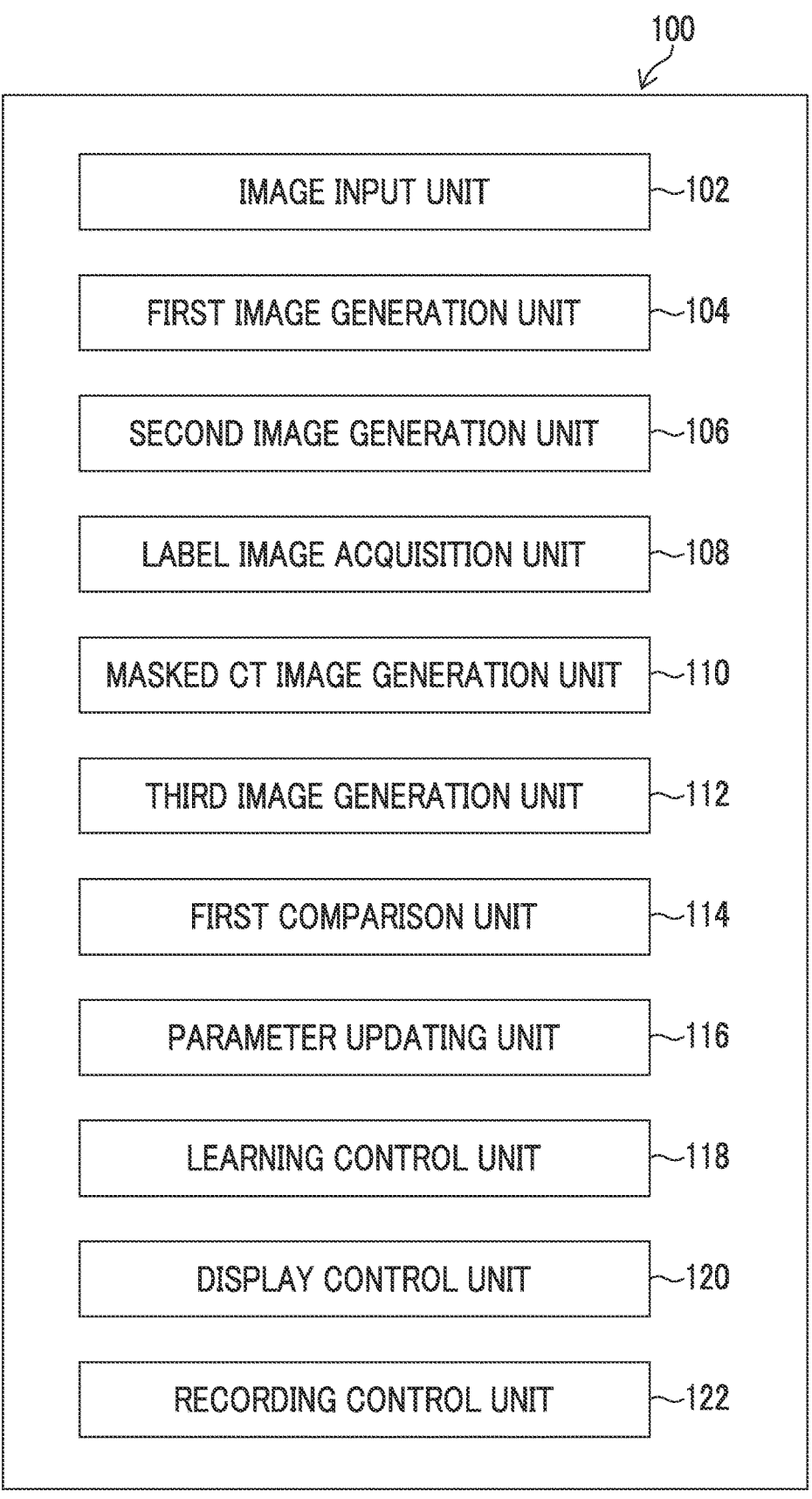
FIG. 2 is a diagram showing a functional configuration of a processor.

FIG. 2 is a diagram showing a functional configuration of the processor 100. As shown in the drawing, the processor 100 comprises an image input unit 102, a first image generation unit 104, a second image generation unit 106, a label image acquisition unit 108, a masked CT image generation unit 110, a third image generation unit 112, a first comparison unit 114, a parameter updating unit 116, a learning control unit 118, a display control unit 120, and a recording control unit 122. Learning in the learning apparatus 10 is performed primarily using the image input unit 102 to the learning control unit 118. The display control unit 120 displays various images (simple X-ray image, pseudo X-ray image, three-dimensional CT image, and the like) on the display device 300, and the recording control unit 122 controls recording of images or data from the storage device 200 or to the storage device 200.

The above-described functions of the processor 100 can be realized by using various processors and a recording medium. Various processors include, for example, a central processing unit (CPU) that is a general-purpose processor that executes software (program) to realize various functions and a programmable logic device (PLD) that is a processor whose circuit configuration can be changed after manufacture, such as a graphics processing unit (GPU), which is a processor specialized in image processing, and a field programmable gate array (FPGA). Each function may be realized by one processor, or may be realized by a plurality of processors of the same type or different types (for example, a plurality of FPGAs, a combination of a CPU and an FPGA, or a combination of a CPU and a GPU). In addition, a plurality of functions may be realized by one processor. The hardware structure of various processors is, more specifically, an electric circuit (circuitry), in which circuit elements, such as semiconductor elements, are combined.

In a case where the processor or the electric circuit described above executes software (program), a code of software to be executed that is readable by a computer (for example, various processors or electric circuits that configure the processor 100 and/or a combination thereof) is stored in a non-transitory recording medium (memory), such as a flash memory or a read only memory (ROM) (not shown), and the computer refers to software. The program to be executed includes a program (learning program and image processing program) that executes a method (learning method and image processing method) according to one aspect of the present invention. During the execution of software, information (image and other kinds of data) stored in the storage device 200 is used as necessary. During the execution, for example, a random access memory (RAM) (not shown) is used as a transitory storage region.

[Information Stored in Storage Device]

The storage device 200 (memory) is configured with various magnetooptical recording mediums or semiconductor memories and control units thereof, and stores a CT image or an X-ray image (simple X-ray image, real X-ray image) acquired by actually imaging a subject, a pseudo X-ray image (first to fifth pseudo X-ray images) generated in a pseudo manner, software (including the learning program and the image processing program according to the aspect of the present invention) that is executed by the above-described processor, and the like.

[Configuration of Display Device, Operation Unit, and Communication Unit]

The display device 300 is configured with a device, such as a liquid crystal monitor, and can display a CT image, an X-ray image, a result of learning or image processing, and the like. In addition, the operation unit 400 is configured with a mouse, a keyboard, or the like (not shown), and a user can give an instruction required for executing the medical-use image processing method or the learning method via the operation unit 400. The user can give the instruction via a screen displayed on the display device 300. The display device 300 may be configured by a touch panel type monitor, and the user may give the instruction via the touch panel. The communication unit 500 can acquire CT images, X-ray images, and other kinds of information from another system connected thereto via a network (not shown).

[Learning Method by Learning Apparatus]

Next, a learning method (machine learning method) by the learning apparatus 10 will be described. FIG. 3 is a diagram showing a manner of learning in the first embodiment. Various images in FIG. 3 are indicated by solid-line frames, and processing on the images is indicated by dotted-line frames (the same applies to the drawings described below).

[Input of Image]

Figure 4:
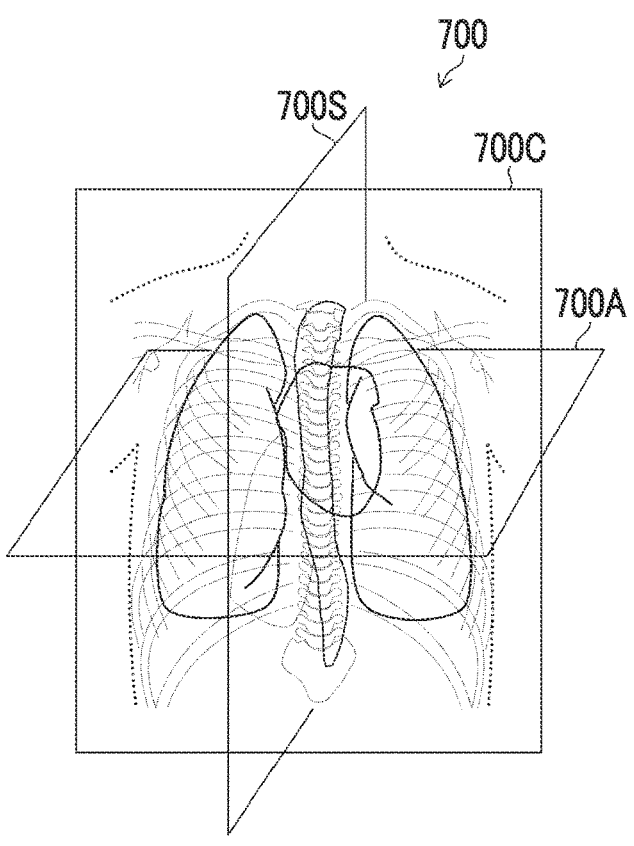
FIG. 4 is a diagram schematically showing a three-dimensional CT image.

The image input unit 102 (processor) input a three-dimensional CT image of a subject (Step S100; image input step, image input processing). FIG. 4 is a diagram schematically showing a three-dimensional CT image 700 (three-dimensional CT image, X-ray CT image), and shows a lung, a heart, and a main artery as anatomical regions. In the three-dimensional CT image 700, cross sections 700S, 700C, and 700A are cross sections in a sagittal direction, a coronal direction, and an axial direction, respectively.

[Generation of First Pseudo X-Ray Image]

Figure 5:
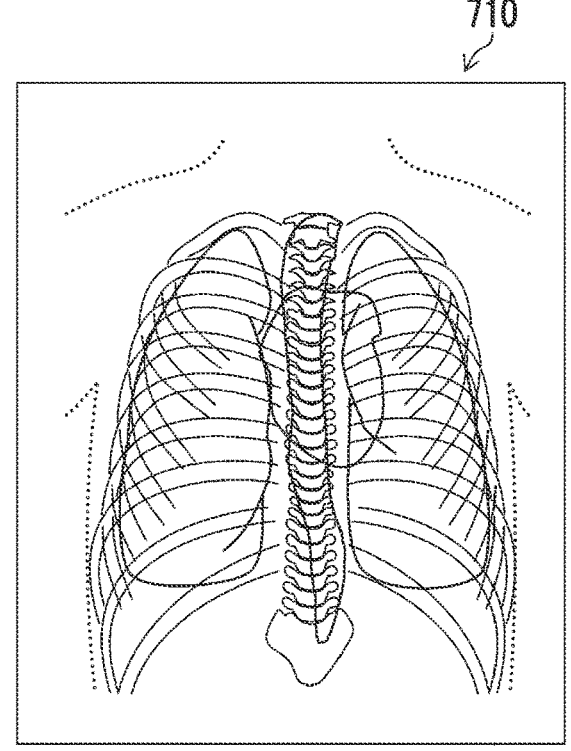
FIG. 5 is a diagram schematically showing a first pseudo X-ray image.

The first image generation unit 104 (processor) projects the three-dimensional CT image 700 into a two-dimensional space to generate a first pseudo X-ray image (Step S102; first image generation step, first image generation processing). The first image generation unit 104 can perform image projection by various known methods. FIG. 5 is a diagram schematically showing the first pseudo X-ray image. The first pseudo X-ray image is a non-decomposed image in which a plurality of anatomical regions (in FIG. 5, bone, lung, heart, and main artery) are shown collectively.

[Generation of Second Pseudo X-Ray Image]

Figure 6:
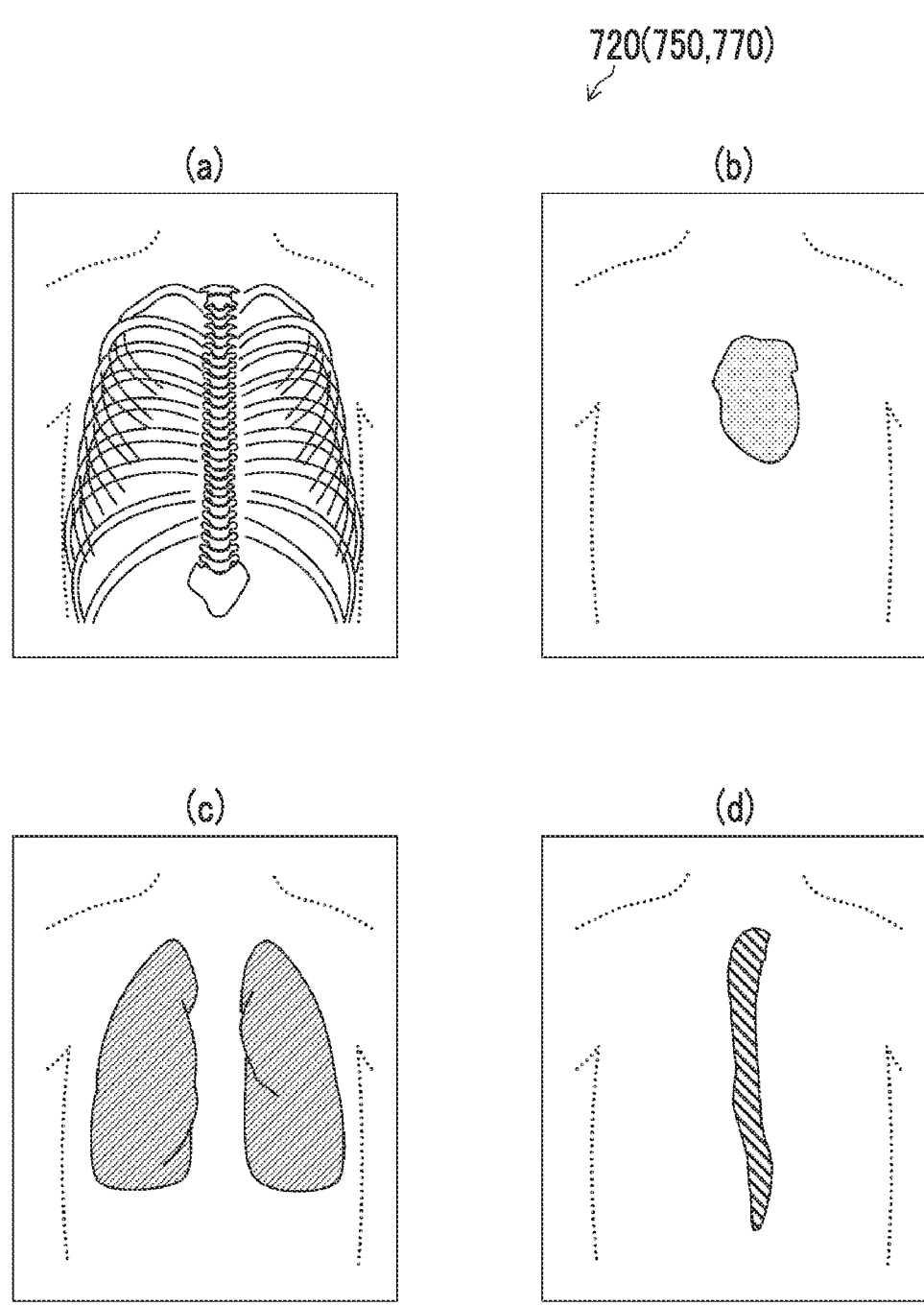
FIG. 6 is a diagram schematically showing second to fourth pseudo X-ray images.

The second image generation unit 106 (processor) generates, from the first pseudo X-ray image 710, a second pseudo X-ray image 720 (second pseudo X-ray image) that is a plurality of images (decomposed image) in which a plurality of anatomical regions of the subject are respectively decomposed and shown (Step S104; second image generation step, second image generation processing). FIG. 6 is a diagram showing an example of a pseudo X-ray image, and a portion (a) to a portion (d) of FIG. 6 are images in which a bone, a heart, a lung, and a main artery are shown, respectively. A third pseudo X-ray image 750 and a fourth pseudo X-ray image 770 described below are also images in which a bone, a heart, a lung, and a main artery are shown as in FIG. 6.

The second image generation unit 106 is a generator or a converter that receives the input of the first pseudo X-ray image 710 and generates the second pseudo X-ray image 720, and can be configured using a method of machine learning, such as deep learning. Specifically, the second image generation unit 106 can be configured using a neural network, such as U-Net (a kind of a fully convolution network (FCN)) that is used in a convolutional neural network (CNN), a support vector machine (SVM), or pix2pix, for example. A ResNet (Deep Residual Network)-based neural network may be used. The neural networks are an example of the configuration of the second image generation unit 106, and are not intended to limit to a method that is used for image generation or conversion in an aspect of the present invention.

An example of a layer configuration in a case where the second image generation unit 106 is configured with the CNN will be described. The CNN includes an input layer, an intermediate layer, and an output layer. The input layer receives the first pseudo X-ray image 710 and outputs a feature quantity. The intermediate layer includes convolutional layers and pooling layers, and receives the feature quantity output from the input layer and calculates another feature quantity. These layers have a configuration in which a plurality of "nodes" are connected by "edges" and hold a plurality of weight parameters. The value of the weight parameter changes as the learning progresses. The output layer outputs a recognition result regarding to which of anatomical regions (in the present example, a bone, a heart, a lung, and a main artery) each pixel of the input image belongs, based on the feature quantity output from the intermediate layer. In regard to the output, only pixels belonging to a specific anatomical region are made as one image, so that an image of each anatomical region shown in FIG. 6 can be obtained.

[Generation of Third Pseudo X-Ray Image]

Figure 7:
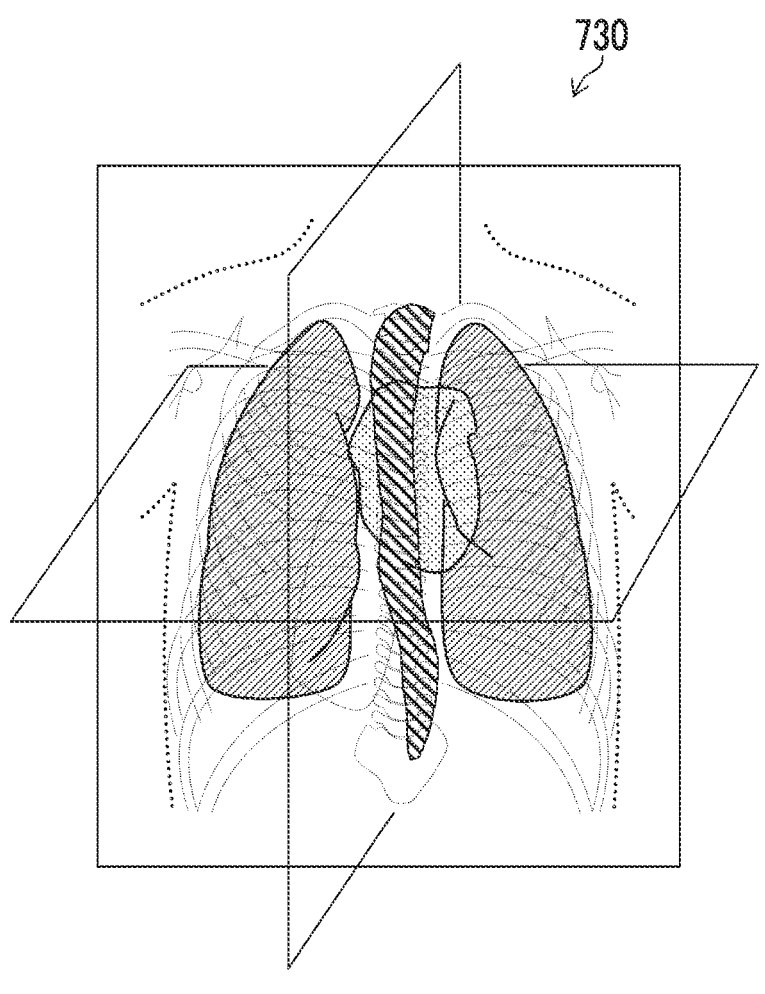
FIG. 7 is a diagram schematically showing a label image.

The label image acquisition unit 108 (processor) extracts a plurality of anatomical regions of the subject from the three-dimensional CT image 700, performs labeling for each pixel, for example (region extraction), and acquires an extracted CT image 730 (three-dimensional image; a label image in which a plurality of anatomical regions are labeled) (Step S108; label image acquisition step, label image acquisition processing). FIG. 7 is a diagram schematically showing a label image, and labels respectively attached to different anatomical regions are shown in different shaded states.

The label image acquisition unit 108 can perform labeling using a known image processing method. The label image acquisition unit 108 may acquire an image subjected to labeling in advance (may be an image subjected to labeling by an apparatus other than the learning apparatus 10 or an image subjected to labeling based on a user operation).

The masked CT image generation unit 110 (processor) generates a masked CT image that is a three-dimensional image in which a plurality of anatomical regions are respectively decomposed and shown, based on the three-dimensional CT image 700 and the extracted CT image 730 (label image) (Step S110; masked CT image generation step, masked CT image generation processing).

In Step S110, the masked CT image generation unit 110 generates a mask image from the extracted CT image 730. The mask image is, for example, a three-dimensional image where pixel values of the pixels belonging to the specific anatomical region are 1 and pixel values of other regions are 0 (zero). The masked CT image generation unit 110 creates the mask image for each anatomical region. Then, the masked CT image generation unit 110 multiples the extracted CT image 730 and the mask image for each anatomical region, thereby generating a masked CT image that is a three-dimensional image in which a plurality of anatomical regions are respectively decomposed and shown.

Figure 8A:
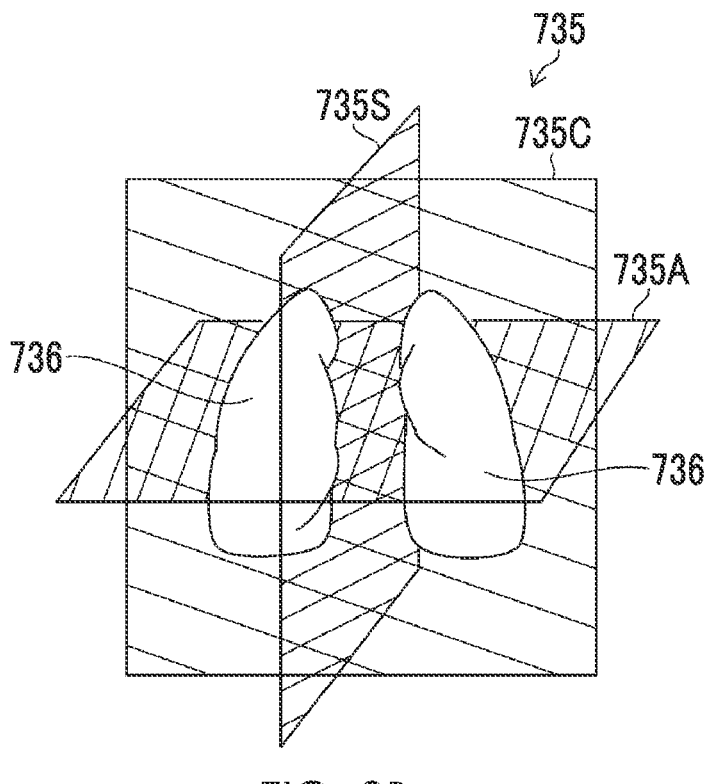
FIGS. 8A and 8B are diagrams showing a manner of generating a masked CT image.
Figure 8B:
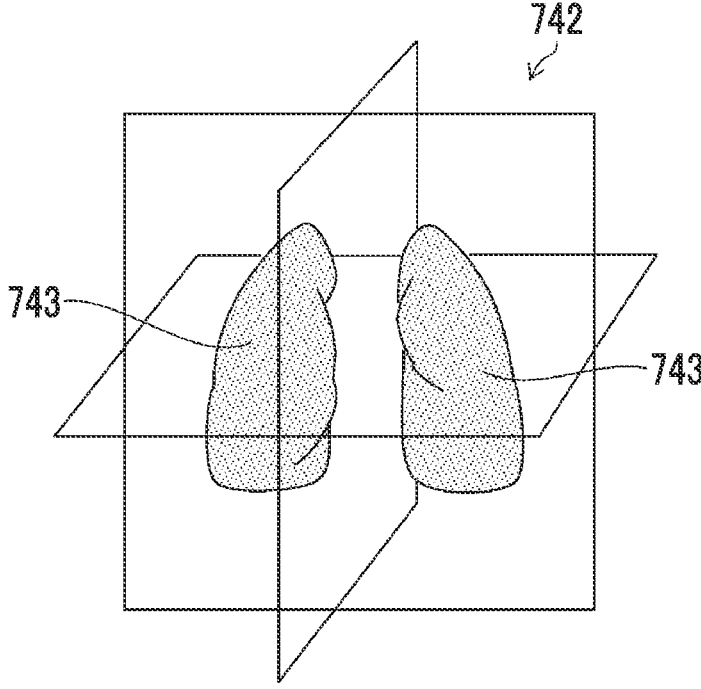

FIGS. 8A and 8B are diagrams showing a manner of generating a masked CT image. FIG. 8A shows a mask image 735 of a lung region 736, and in this image, a pixel value of a lung region 736 is 1, and pixel values of other regions are 0 (zero). In FIGS. 8A and 8B, regions where the pixel value is 0 are hatched. Cross sections 735S, 735C, and 735A are cross sections in a sagittal direction, a coronal direction, and an axial direction, respectively. FIG. 8B shows a masked CT image 742 of a lung generated by multiplying the three-dimensional CT image 700 by the mask image 735, and only a lung region 743 out of the three-dimensional CT image 700 is extracted.

The masked CT image generation unit 110 can generate a masked CT image 740 that is a three-dimensional image in which a plurality of anatomical regions are respectively decomposed and shown, by executing the same processing on other anatomical regions, such as a bone, a heart, and a main artery, as well as the lung.

The third image generation unit 112 (processor) projects the masked CT image 740 into a two-dimensional space to generate a third pseudo X-ray image 750 that is a plurality of images in which a plurality of anatomical regions are respectively decomposed and shown (Step S112; third image generation step, third image generation processing). The third pseudo X-ray image 750 is a plurality of two-dimensional images in which the same anatomical regions as the above-described second pseudo X-ray image 720 are decomposed (as described below, for comparison of the second pseudo X-ray image 720 and the third pseudo X-ray image 750, decomposition is performed on the same anatomical regions).

[Image Comparison]

The first comparison unit 114 (processor) compares the second pseudo X-ray image 720 and the third pseudo X-ray image 750 (Step S106; first comparison step, first comparison processing). The first comparison unit 114 can perform image comparison by taking a difference in pixel value for each pixel and adding or weighting and adding the difference.

[Parameter Update]

The parameter updating unit 116 (processor) updates a value of a parameter for use in generating the second pseudo X-ray image 720 in the second image generation unit 106 based on a result of the comparison of Step S106 (Step S114; updating step, updating processing). The parameter updating unit 116 can calculate an error of the second pseudo X-ray image 720 with respect to the third pseudo X-ray image 750 as a reference in Step S106 (first comparison step), for example, and can reduce the error by updating the parameter in Step S114 (updating step). Such a method corresponds to learning without using a configuration, such as a generative adversarial network (GAN).

In the learning according to the first embodiment, the parameter may be updated in view of a discrimination result, in addition to the error of the image. In this case, the parameter updating unit 116 (or the first comparison unit 114) may calculate an error of the second pseudo X-ray image 720 with respect to the third pseudo X-ray image 750 as a reference in Step S106 (first comparison step), for example, may discriminate the third pseudo X-ray image 750 and the second pseudo X-ray image 720, may integrate the error and a discrimination result, and may reduce an integration result by updating the parameter in Step S114 (updating step). Such a method corresponds to learning using a conditional GAN (a case where an unpaired discriminator is used).

In the learning according to the first embodiment, the parameter may be updated in view of a discrimination result of pair data, in addition to the error of the image. In this case, the parameter updating unit 116 (or the first comparison unit 114) may calculate an error of the second pseudo X-ray image 720 with respect to the third pseudo X-ray image 750 as a reference in Step S106 (first comparison step), for example, may discriminate pair data of the first pseudo X-ray image 710 and the third pseudo X-ray image 750 and pair data of the first pseudo X-ray image 710 and the second pseudo X-ray image 720, may integrate the error and a discrimination result, and may reduce an integration result by updating the parameter in Step S114 (updating step). Such a method corresponds to learning using a conditional GAN (a case where a paired discriminator is used).

[Image Discrimination and Integration with Comparison Result]

In the "discrimination" of the images described above, determination about "whether images are the same or different" or "whether images are real or false" can be performed. Note that there is a variation in a discrimination method for "each image" or "each batch". The latter is called a "batch discriminator", and has been suggested in "Image-to-Image Translation with Conditional Adversarial Networks", ICCV, 2017, Philip Isola et al., [Searched on Jun. 24, 2021], Internet (https://openaccess.thecvf.com/content_cvpr_2017/papers/Isola_Image-To-Image_Translation_With_CVPR_2017_paper.pdf).

In the "image comparison" like Step S106, for example, the first comparison unit 114 calculates an absolute value error (or a square error or the like) for each pixel, calculates an average (or a sum or the like), and outputs a scalar value. On the other hand, in the "image discrimination" or the "pair data discrimination", for a batch discriminator, a classification error about "whether real or false" for each batch is calculated, an average (or a sum or the like) is calculated, and a scalar value is output. Then, in the above-described "integration", the parameter updating unit 116 (or the first comparison unit 114) calculates a weighted sum (a result of integration) of the scalar values. The parameter updating unit 116 reduces the weighted sum by updating the parameter.

The image comparison or discrimination, and the result integration described above can be performed in the same manner in second and third embodiments described below (for example, see Steps S106, S116, and S118 of FIG. 10, and Steps S106, S122, and S124 of FIG. 14).

[Control of Learning]

The learning control unit 118 (processor) causes each unit of the processor 100 to repeat the processing of Step S100 to Step S114 until a predetermined condition is satisfied. Learning (parameter update) proceeds with repetition of such processing. In the repetition of the processing, for example, various methods, such a serial processing, batch processing, and mini batch processing, can be used. As the "predetermined condition" for ending learning (parameter update), the number of times of update of the parameter, the comparison result satisfying a reference, the end of the processing on all images, or the like can be used.

In a case where learning ends in such a manner (in a case where the "predetermined condition" is satisfied and the update of the parameter ends), as described below, the two-dimensional X-ray image can be decomposed into a variety of regions using the second image generation unit 106 and the updated parameter. That is, the second image generation unit 106 in a state in which learning ends can be ascertained as a "trained model".

Second Embodiment

A second embodiment of a learning method, a learning apparatus, and a learning program of the present invention will be described. FIG. 9 is a diagram showing a functional configuration of a processor 100A (processor) in the second embodiment. The processor 100A has a fourth image generation unit 124 and an image discrimination unit 126, in addition to the functions (the image input unit 102 to the recording control unit 122) of the processor 100 in the first embodiment. In the second embodiment, the same components and processing contents as those in the first embodiment are represented by the same reference numerals, and detailed description will not be repeated.

[Learning in Second Embodiment]

Figure 10:
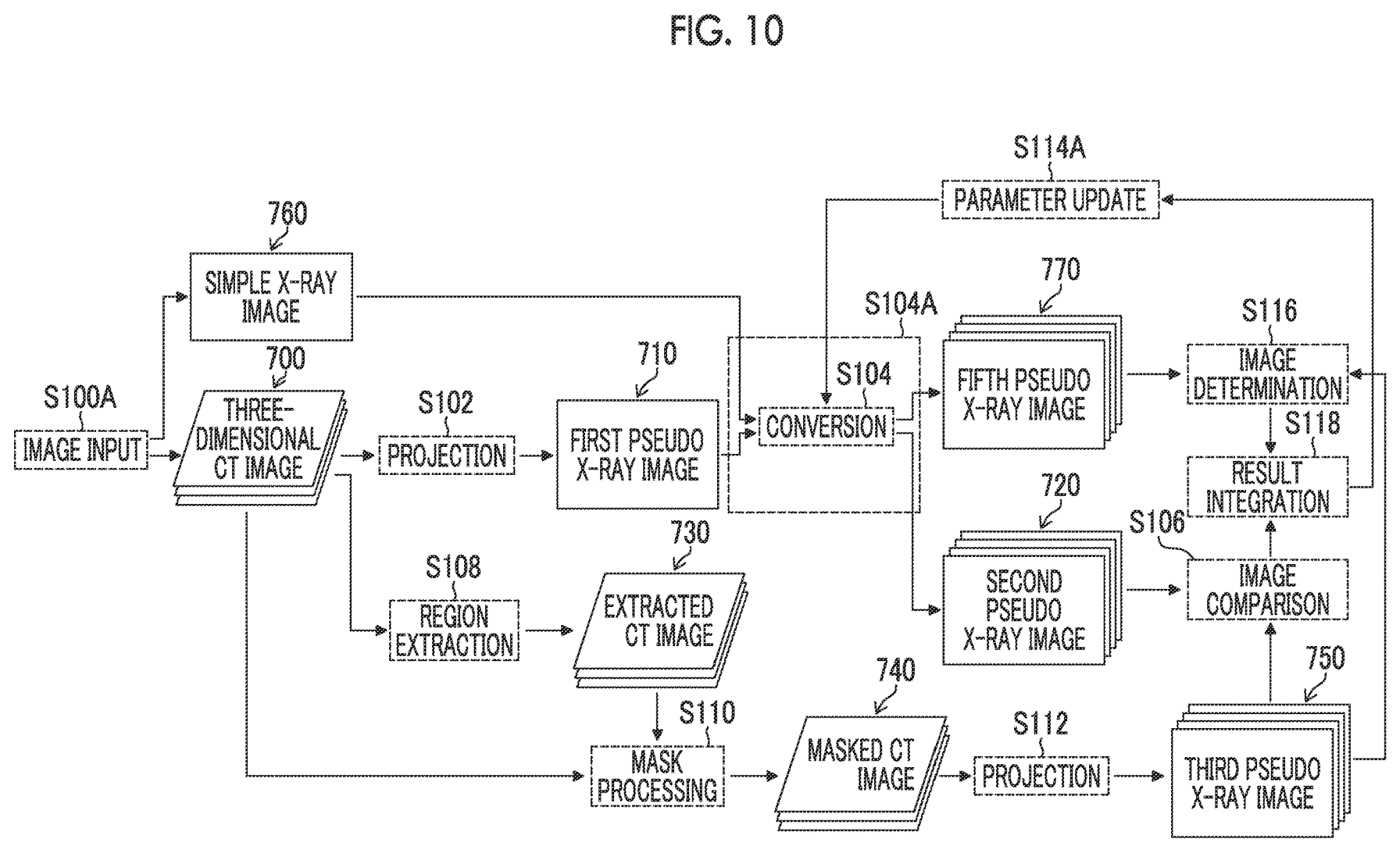

FIG. 10 is a diagram showing a manner of learning in the second embodiment. In the second embodiment, in addition to the three-dimensional CT image 700, a simple X-ray image 760 is used for learning.

Figure 11:
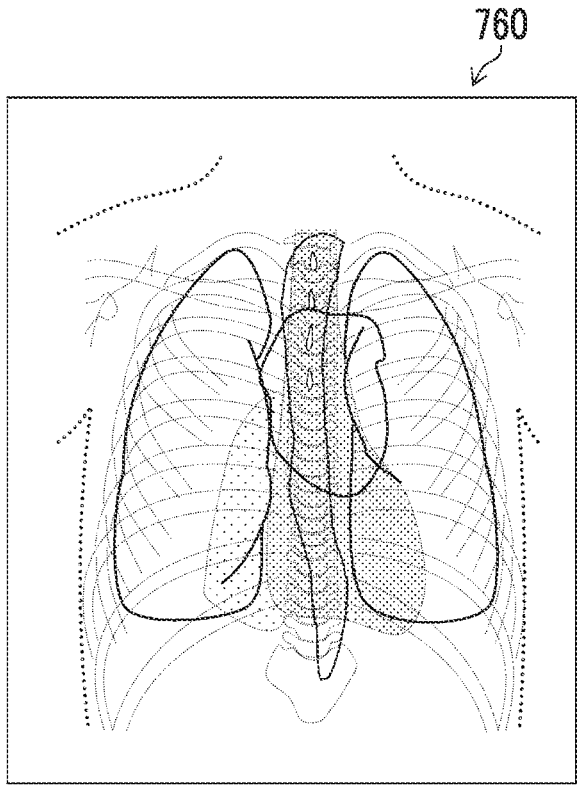
FIG. 11 is a diagram schematically showing a simple X-ray image.

The image input unit 102 further inputs the simple X-ray image 760 (simple X-ray image), in addition to the three-dimensional CT image 700 (Step S100A; image input step, image input processing). The simple X-ray image 760 is a two-dimensional real image obtained by actually imaging the subject as shown in a schematic view of FIG. 11.

[Reduction of Domain Shifting]

The simple X-ray image is often captured in an upright posture, and the three-dimensional CT image is often captured in a supine posture. For this reason, processing of reducing domain shifting between the three-dimensional CT image 700 and the simple X-ray image 760 may be executed. Reduction of domain shifting can be performed using, for example, the following methods (medical-use image processing methods).

(Method 1)

A medical-use image processing method processor that is executed by a medical-use image processing apparatus including a processor, in which the processor is configured to execute, a reception step of receiving an input of a first medical-use image actually captured in a first posture, and an image generation step of generating, from the first medical-use image, a second medical-use image in which the same part as in the first medical-use image is captured in a second posture different from the first posture, in a pseudo manner, the second medical-use image being generated using a deformation vector field for converting the first medical-use image into the second medical-use image.

It is preferable that, in the image generation step of the above-described method, the processor is configured to generate the deformation vector field using a generator that outputs the deformation vector field in a case where the first medical-use image is input, and is trained by machine learning. It is preferable that, in the image generation step, the processor is configured to apply the deformation vector field to the first medical-use image to generate the second medical-use image. The processor may be configured to further execute a modality conversion step of converting the second medical-use image generated in a pseudo manner into a third medical-use image by a modality different from the second medical-use image in a pseudo manner.

In the above-described method, for example, the first medical-use image can be a three-dimensional CT image (first posture; supine posture) actually captured in a supine posture, and the second medical-use image can be a pseudo CT image (second posture; upright posture) in an upright posture. The third medical-use image can be a pseudo X-ray image in an upright posture. The "deformation vector field" is a set of vectors indicating displacement (image deformation) from each voxel (or pixel) of the first medical-use image to each voxel of the second medical-use image.

As the "processor" in the above-described method, the processor 100A can be used. The "generation unit" in the above-described method can be configured using a neural network as in the second image generation unit 106.

While it is preferable that the simple X-ray image 760 and the three-dimensional CT image 700 are images of the same subject, an aspect of the present invention can be applied to even a case where both are images of different subjects. The reason is that, in general, it is rare to actually acquire images in different postures for the same part of the same subject. It is preferable that the simple X-ray image 760 and the three-dimensional CT image 700 are images of the same part.

[Generation of Fourth Pseudo X-Ray Image]

As described above regarding the first embodiment, the second image generation unit 106 generates the second pseudo X-ray image 720 from the first pseudo X-ray image 710 (Step S104). In the second embodiment, the fourth image generation unit 124 (processor) generates, from the simple X-ray image 760, a fourth pseudo X-ray image 770 (fourth pseudo X-ray image) that is a plurality of images (decomposed image) in which a plurality of anatomical regions (the same anatomical regions as in the second pseudo X-ray image 720) of the subject are respectively decomposed and shown (Step S104A; fourth image generation step, fourth image generation processing). The fourth image generation unit 124 can be configured using a method of machine learning, such as deep learning, as in the second image generation unit 106, and can use the same network configuration and the same parameter (weight parameter or the like) as the second image generation unit 106. That is, the fourth image generation unit 124 can be identified as the second image generation unit 106.

[Image Discrimination]

The image discrimination unit 126 (processor) discriminates the third pseudo X-ray image 750 and the fourth pseudo X-ray image 770 described above (Step S116; discrimination step, discrimination processing). Specifically, the image discrimination unit 126 is about to discriminate (identify) the third pseudo X-ray image 750 and the fourth pseudo X-ray image as "correct answer images", and operates like a discriminator in a generative adversarial network (GAN).

[Parameter Update]

The parameter updating unit 116 (processor) integrates a result of the comparison in Step S106 and a result of the discrimination in Step S116 (Step S118; first integration step, first integration processing), and updates the parameter that is used by the second image generation unit 106 and the fourth image generation unit 124, based on an integration result (Step S114A; updating step, updating processing). For example, the parameter updating unit 116 prevents the image discrimination unit 126 from discriminating the third pseudo X-ray image 750 and the fourth pseudo X-ray image by updating the value of the parameter. That is, the second image generation unit 106 and the fourth image generation unit 124 operate as a generator in the GAN. As in the above-described first embodiment, the second image generation unit 106 and the fourth image generation unit 124 in a state in which learning ends can be ascertained as a "trained model".

In this way, in the second embodiment, the value of the parameter is updated further based on the result of the discrimination, whereby it is possible to perform the generation of the decomposed image described below can be performed with excellent accuracy.

Modification Example of Second Embodiment

Figure 12:
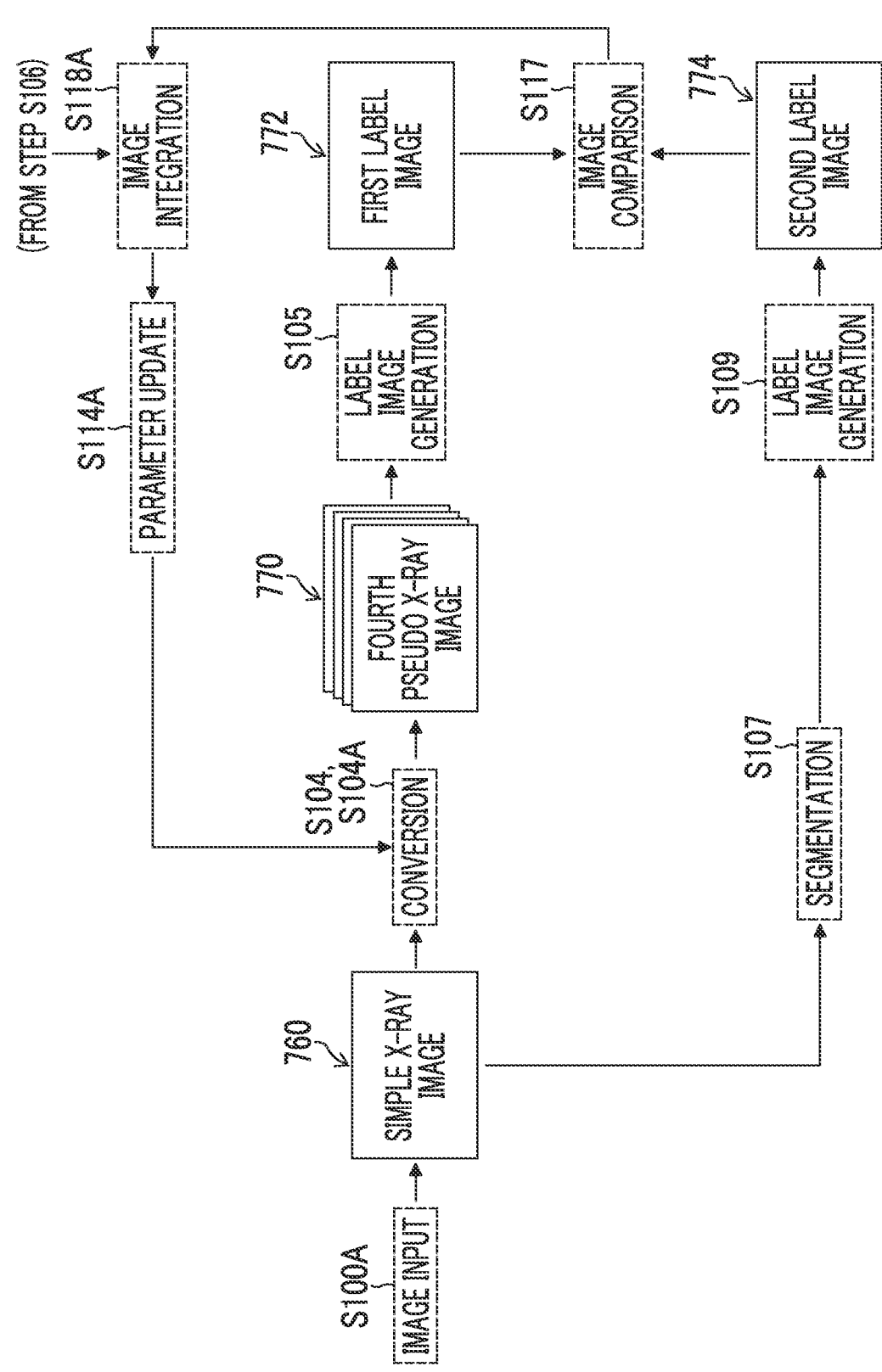
FIG. 12 is a diagram showing a manner of learning in a modification example.

A modification example of the above-described second embodiment will be described. In the second embodiment, although the fourth pseudo X-ray image 770 generated from the simple X-ray image 760 is used for learning, in the present modification example, a labeled image is used for learning. FIG. 12 is a diagram showing a manner of learning in the modification example. In the example shown in the drawing, processing regarding the three-dimensional CT image 700 is as in FIG. 10, and while illustration and detailed description are omitted, the processing of the generation, comparison, and the like of the second pseudo X-ray image 720 and the third pseudo X-ray image 750 is executed as in FIG. 10.

In the modification example shown in FIG. 12, a label image generation unit (not shown) of the processor 100A generates a first label image 772 (first segmentation label) from the fourth pseudo X-ray image 770 (Step S105; first label acquisition step, first label acquisition processing). On the other hand, the label image generation unit performs segmentation on the simple X-ray image 760 by a method, such as snakes (dynamic outline method) or graph cut (Step S107; segmentation step, segmentation processing), and generates a second label image 774 (second segmentation label) (Step S109; second label acquisition step, second label acquisition processing).

Then, a second comparison unit (not shown) of the processor 100A compares the first label image 772 and the second label image 774 (Step S117; label comparison step, label comparison processing). A comparison result is integrated with the comparison result of the second pseudo X-ray image 720 and the third pseudo X-ray image 750 as in Step S106 of FIG. 10 (Step S118A; first integration step, first integration processing), and the parameter updating unit 116 updates the parameter based on an integration result (Step S114A; updating step, updating processing).

According to the modification example, it is possible to perform learning for decomposing the two-dimensional X-ray image into a variety of regions as in the above-described first and second embodiments. According to the modification example, as in a third embodiment described below, instead of using the dual energy X-ray image, a limit regarding an outer shape of an anatomical region is added using the segmentation label of the simple X-ray image, and an influence of domain shifting due to the posture can be reduced. In Steps S105 and S109 of the modification example, a segmentation label processed by an apparatus other than the learning apparatus 10 or a segmentation label attached by a user may be acquired.

Third Embodiment

A third embodiment of a learning method, a learning apparatus, and a learning program of the present invention will be described. The third embodiment is an aspect where a dual energy X-ray image that is a plurality of X-ray images which are captured with X-rays of different energy levels and in which different anatomical regions of the subject are highlighted is further used.
[Functional Configuration of Processor]

FIG. 13 is a diagram showing a functional configuration of a processor 100B (processor) according to the third embodiment. The processor 100B further has a fourth image generation unit 124, a fifth image generation unit 140, a second comparison unit 142, and a second integration unit 144, in addition to the functions (the image input unit 102 to the recording control unit 122) of the processor 100 in the first embodiment. In the third embodiment, the same components and processing contents as in the first and second embodiments are represented by the same reference numerals, and detailed description will not be repeated.
[Manner of Learning]

Figure 14:
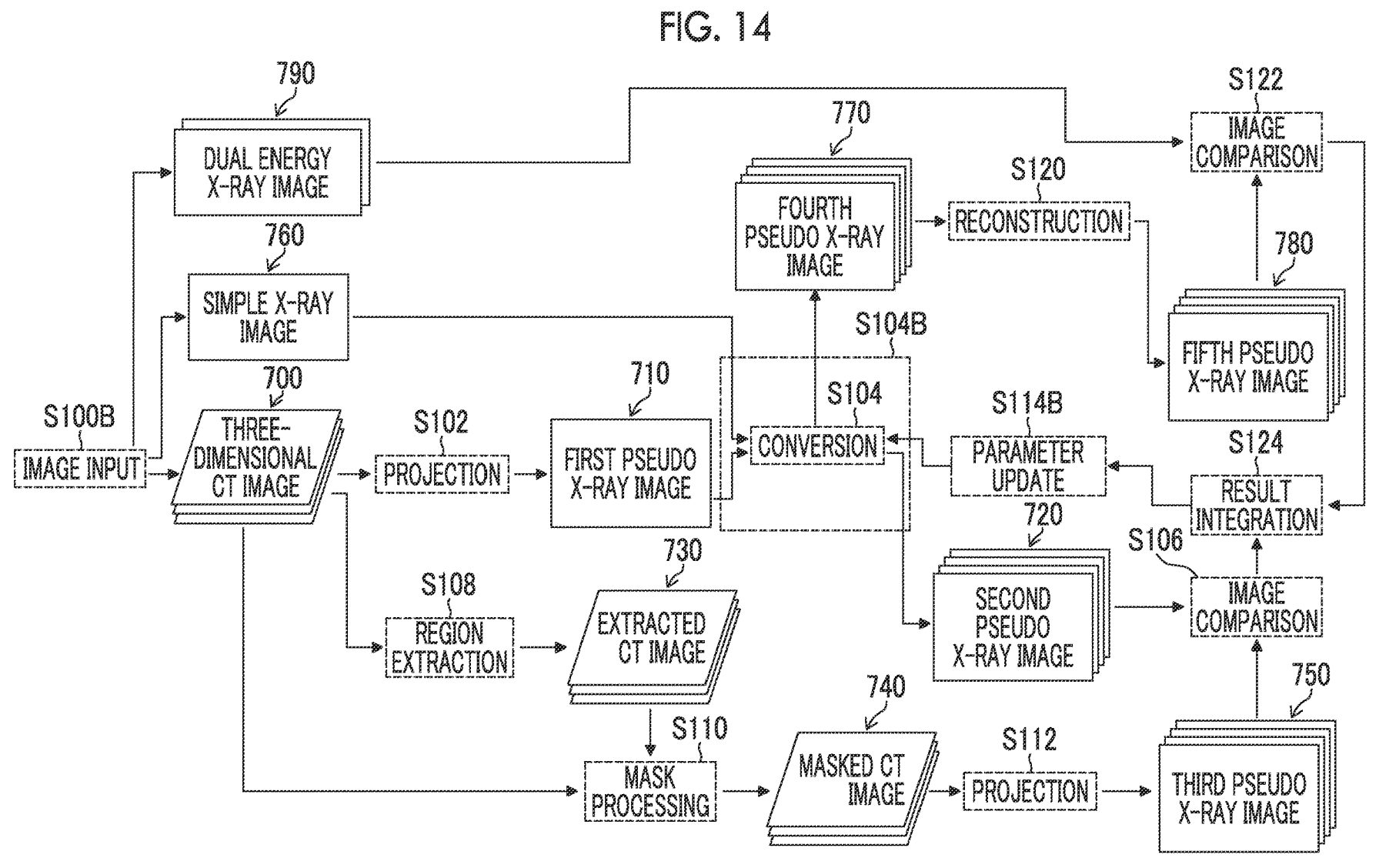

FIG. 14 is a diagram showing a manner of learning in the third embodiment. The image input unit 102 further inputs a simple X-ray image 760 (simple X-ray image) and a dual energy X-ray image 790, in addition to the three-dimensional CT image 700 (Step S100B; image input step, image input processing). As shown in a schematic view of FIG. 11, the simple X-ray image 760 is a two-dimensional image obtained by actually imaging the subject, and the dual energy X-ray image 790 is a plurality of X-ray images which are captured with X-rays of different energy levels and in which different anatomical regions of the subject are highlighted. The simple X-ray image 760 and the dual energy X-ray image 790 can be captured in the same posture (for example, an upright posture). In the dual energy X-ray image 790, for example, as shown in a schematic view of FIG. 15, an image (a portion (a) of the drawing) in which a bone is highlighted and shown and an image (a portion (b) of the drawing) in which a soft tissue is highlighted and shown can be obtained according to the energy level of X-rays for use in imaging.

While it is preferable that the simple X-ray image 760 and the dual energy X-ray image 790 are images of the same subject as the three-dimensional CT image 700, the embodiment of the present invention can be applied to even a case where both images are images of different subjects.

As in the second embodiment, the fourth image generation unit 124 (processor) acquires the fourth pseudo X-ray image (Step S104B; fourth image generation step, fourth image generation processing). As described above regarding the second embodiment, the fourth image generation unit 124 can be configured using a method of machine learning, such as deep learning, as in the second image generation unit 106, and can use the same network configuration and the same parameter (weight parameter or the like) as in the second image generation unit 106. That is, the fourth image generation unit 124 can be identified as the second image generation unit 106.

The fifth image generation unit 140 (processor) reconstructs the fourth pseudo X-ray image 770 to generate a fifth pseudo X-ray image 780 that is a plurality of images in which the same anatomical regions as the X-ray image composing the dual energy X-ray image are highlighted (Step S120; fifth image generation step, fifth image generation processing). Specifically, for example, in a case where the fourth pseudo X-ray image 770 is images of a bone, a heart, a lung, and a main artery as shown in the schematic view of FIG. 6, and the dual energy X-ray image 790 is images of a bone and a soft tissue as shown in the schematic view of FIG. 15, the fifth image generation unit 140 generates an image of the bone and an image of the soft tissue as the fifth pseudo X-ray image 780 conforming to a manner of decomposition of the dual energy X-ray image 790.

The second comparison unit 142 (processor) compares the dual energy X-ray image 790 and the fifth pseudo X-ray image 780 (Step S122; second comparison step, second comparison processing), and the second integration unit 144 (processor) integrates a comparison result with a result of the comparison (the comparison of the third pseudo X-ray image and the second pseudo X-ray image) in Step S106 described above (Step S124; second integration step, second integration processing). The second integration unit 144 can perform the integration of the comparison results by simple addition, weighted addition, or the like.

The dual energy X-ray image 790 and the fifth pseudo X-ray image 780 are decomposed images of "bone and soft tissue", for example, and in a case where such images are compared, the second comparison unit 142 (processor) calculates an absolute value error (or a square error or the like) for each pixel in each of "bone" and "soft tissue", calculates an average (or a sum or the like), and outputs a scalar value. The second comparison unit 142 averages the scalar values in "bone" and "soft tissue", and calculates a final scalar value.

On the other hand, the second pseudo X-ray image 720 and the third pseudo X-ray image 750 are decomposed images of "bone, lung, heart, and main artery", for example. In the comparison (Step S106) of such images, the parameter updating unit 116 (or the first comparison unit 114) calculates scalar values as in "bone and soft tissue", and the second integration unit 144 (processor) calculates, for example, a weighted sum (integrated result of comparison) of the scalar values. The "weight" herein is a hyperparameter that is empirically decided, not a learning parameter.

The parameter updating unit 116 (processor) updates the parameter for use in generating the pseudo X-ray image in the second image generation unit 106 based on the integrated result of the comparison (Step S114B; updating step, updating processing). The parameter updating unit 116 can bring the fifth pseudo X-ray image 780 close to the dual energy X-ray image 790 by updating the parameter.

A method using the pseudo X-ray image generated from the three-dimensional CT image can perform decomposition into multiple regions as well as the bone and the soft tissue, and on the other hand, in the method using the dual energy X-ray image, domain shifting due to the posture does not occur (because imaging can be performed in the same posture as the simple X-ray image). In the third embodiment, the dual energy X-ray image and the pseudo X-ray image are complementarily combined in this way, so that it is possible to perform learning for decomposing the two-dimensional X-ray image into a variety of regions while reducing domain shifting due to an imaging posture. As in the first and second embodiments, the second image generation unit 106 in a state in which learning ends can be ascertained as a trained model.
[Application to Image Processing]

The learning method, the learning apparatus, and the learning program according to an aspect of the present invention can be applied to image processing (image processing method, image processing apparatus, and image processing program). Specifically, the parameter updated by learning described in the first to third embodiments is applied, and the two-dimensional X-ray image is input to the second image generation unit 106 (processor, converter), so that it is possible to obtain a decomposed image in which the two-dimensional X-ray image is decomposed into a variety of regions.

Figures 15, 16:
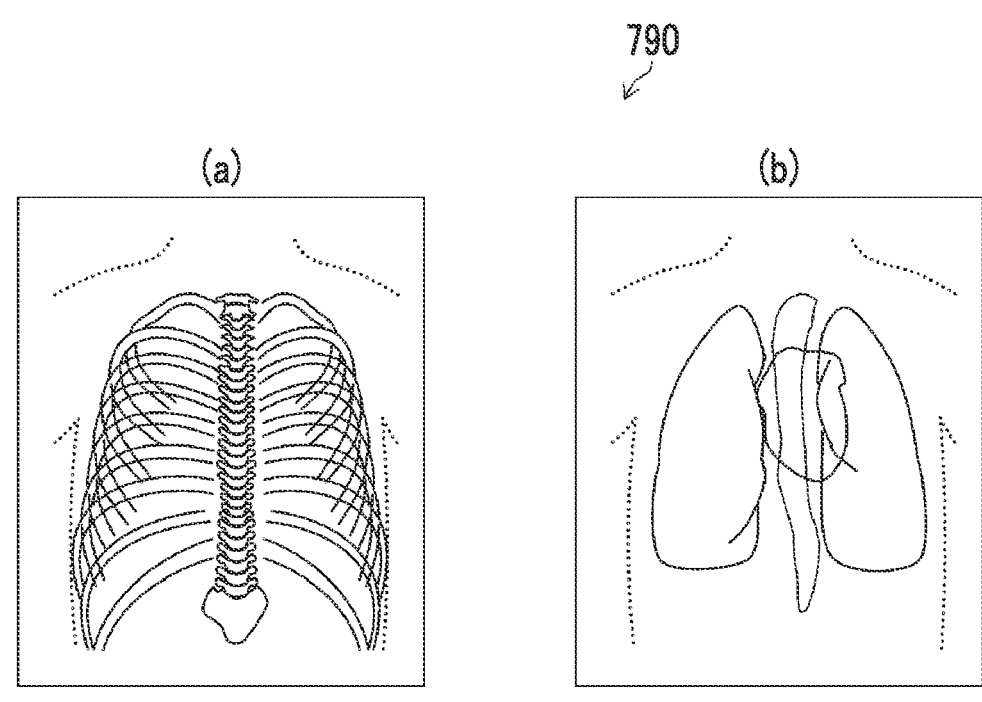
FIG. 15 is a diagram schematically showing a dual energy X-ray image.
FIG. 16 is a diagram showing a manner of image processing using a learning result.

FIG. 16 is a diagram showing an example where a decomposed image is generated. In the example shown in FIG. 16, the simple X-ray image 760 is input to the second image generation unit 106 (processor, converter, trained model) in a state in which learning ends, so that a decomposed image (corresponding to the second pseudo X-ray image 720) is generated (Step S114; decomposed image generation step, decomposed image generation processing). The pseudo X-ray image, not the simple X-ray image 760 (real X-ray image), may be input.

In this way, the learning apparatus 10 in a state in which learning ends is also operable as an image processing apparatus that generates a decomposed image. On the other hand, the second image generation unit 106 in a state in which learning ends is transplanted to an image processing apparatus separated from the learning apparatus 10 (the same network configuration and the same parameter are used), so that it is also possible to configure an image processing apparatus that generates a decomposed image. In such an image processing apparatus, a decomposed image can be generated by an image processing method and an image processing program according to an aspect of the present invention.

The image processing method, the image processing apparatus, and the image processing program according to an aspect of the present invention can be applied to even image segmentation. Specifically, the processor, such as the second image generation unit 106 (processor, converter, trained model), can convert the decomposed image into a segmentation label (label acquisition step, label acquisition processing).

The embodiments of the present invention have been described above, but the present invention is not limited to the aspects described above, and can have various modifications without departing from the gist of the present invention.

EXPLANATION OF REFERENCES

10: learning apparatus
100: processor
100A: processor
100B: processor
102: image input unit
104: first image generation unit
106: second image generation unit
108: label image acquisition unit
110: masked CT image generation unit
112: third image generation unit
114: first comparison unit
116: parameter updating unit
118: learning control unit
120: display control unit
122: recording control unit
124: fourth image generation unit
126: image discrimination unit
140: fifth image generation unit
142: second comparison unit

144: second integration unit
200: storage device
300: display device
400: operation unit
500: communication unit
700: three-dimensional CT image
700A: cross section
700C: cross section
700S: cross section
710: first pseudo X-ray image
720: second pseudo X-ray image
730: CT image
735: mask image
735A: cross section
735C: cross section
735S: cross section
736: lung region
740: masked CT image
742: masked CT image
743: lung region
750: third pseudo X-ray image
760: simple X-ray image
770: fourth pseudo X-ray image
772: first label image
774: second label image
780: fifth pseudo X-ray image
790: dual energy X-ray image
S100 to S124: each step of learning method and image processing method

What is claimed is:

1. A learning method comprising:
inputting a three-dimensional CT image of a subject;
projecting the three-dimensional CT image into a two-dimensional space to generate a first pseudo X-ray image;
generating, from the first pseudo X-ray image, a second pseudo X-ray image that is a plurality of images in which a plurality of anatomical regions of the subject are respectively decomposed and shown;
acquiring a label image in which the plurality of anatomical regions are labeled to the three-dimensional CT image;
generating a masked CT image that is a three-dimensional image in which the plurality of anatomical regions are respectively decomposed and shown, based on the three-dimensional CT image and the label image;
projecting the masked CT image into a two-dimensional space to generate a third pseudo X-ray image that is a plurality of images in which the plurality of anatomical regions are respectively decomposed and shown;
comparing the second pseudo X-ray image and the third pseudo X-ray image;
updating a value of a parameter for use in generating the second pseudo X-ray image based on a result of the comparison; and
repeating the input of the three-dimensional CT image, the generation of the first pseudo X-ray image, the generation of the second pseudo X-ray image, the acquisition of the label image, the generation of the masked CT image, the generation of the third pseudo X-ray image, the comparison of the second pseudo X-ray image and the third pseudo X-ray image, and the update of the value of the parameter until a predetermined condition is satisfied.

2. The learning method according to claim 1,
wherein, in the comparison of the second pseudo X-ray image and the third pseudo X-ray image, an error of the second pseudo X-ray image with respect to the third pseudo X-ray image as a reference is calculated, and in the update of the value of the parameter, the error is reduced by updating the parameter.

3. The learning method according to claim 1, wherein, in the comparison of the second pseudo X-ray image and the third pseudo X-ray image, an error of the second pseudo X-ray image with respect to the third pseudo X-ray image as a reference is calculated, the third pseudo X-ray image and the second pseudo X-ray image are discriminated, and the error and a result of the discrimination are integrated, and in the update of the value of the parameter, a result of the integration is reduced by updating the parameter.

4. The learning method according to claim 1, wherein, in the comparison of the second pseudo X-ray image and the third pseudo X-ray image, an error of the second pseudo X-ray image with respect to the third pseudo X-ray image as a reference is calculated, pair data of the first pseudo X-ray image and the third pseudo X-ray image and pair data of the first pseudo X-ray image and the second pseudo X-ray image are discriminated, and the error and a result of the discrimination are integrated, and in the update of the value of the parameter, a result of the integration is reduced by updating the parameter.

5. The learning method according to claim 1, wherein, in the acquisition of the label image, the label image is acquired by generating the label image from the three-dimensional CT image.

6. The learning method according to claim 1, wherein, in the generation of the masked CT image, a mask image is generated from an extracted CT image obtained by performing region extraction on the three-dimensional CT image, and the extracted CT image is multiplied by the mask image to generate the masked CT image.

7. The learning method according to claim 1, wherein a simple X-ray image is further input in the input of the three-dimensional CT image, a fourth pseudo X-ray image that is a plurality of images in which the plurality of anatomical regions are respectively decomposed and shown is generated from the simple X-ray image, the second pseudo X-ray image and the fourth pseudo X-ray image are discriminated, and in the update of the value of the parameter, the value of the parameter is updated further based on a result of the discrimination of the second pseudo X-ray image and the fourth pseudo X-ray image.

8. The learning method according to claim 7, wherein the fourth pseudo X-ray image is converted into a first segmentation label, a second segmentation label for the simple X-ray image is acquired, the first segmentation label and the second segmentation label are compared, the result of the comparison of the second pseudo X-ray image and the third pseudo X-ray image and a result of the comparison of the first segmentation label and the second segmentation label are integrated, and in the update of the value of the parameter, the parameter is updated based on the integrated result of the comparison.

9. The learning method according to claim 1, wherein, in the input of the three-dimensional CT image, a simple X-ray image and a dual energy X-ray image that is a plurality of X-ray images which are captured with X-rays of different energy levels and in which different anatomical regions of the subject are highlighted are input, a fourth pseudo X-ray image that is a plurality of images in which the plurality of anatomical regions are respectively decomposed and shown is generated from the simple X-ray image, the fourth pseudo X-ray image is reconstructed to generate a fifth pseudo X-ray image that is a plurality of images in which the same anatomical regions as X-ray images composing the dual energy X-ray image are respectively highlighted, the dual energy X-ray image and the fifth pseudo X-ray image are compared, a result of the comparison of the dual energy X-ray image and the fifth pseudo X-ray image is integrated with the result of the comparison of the second pseudo X-ray image and the third pseudo X-ray image, and in the update of the value of the parameter, the parameter is updated based on the integrated result of the comparison.

10. An image processing method comprising:

acquiring a simple X-ray image or a pseudo X-ray image; and converting the acquired simple X-ray image or pseudo X-ray image with a parameter updated by the learning method according to claim 1 to generate a decomposed image that is a plurality of images in which a plurality of anatomical regions of the subject are respectively decomposed and shown.

11. The image processing method according to claim 10, wherein the decomposed image is converted into a segmentation label.

12. A learning apparatus comprising:

a processor, wherein the processor is configured to:

input a three-dimensional CT image of a subject;

project the three-dimensional CT image into a two-dimensional space to generate a first pseudo X-ray image;

generate, from the first pseudo X-ray image, a second pseudo X-ray image that is a plurality of images in which a plurality of anatomical regions of the subject are respectively decomposed and shown acquire a label image in which the plurality of anatomical regions are labeled to the three-dimensional CT image;

generate a masked CT image that is a three-dimensional image in which the plurality of anatomical regions are respectively decomposed and shown, based on the three-dimensional CT image and the label image;

project the masked CT image into a two-dimensional space to generate a third pseudo X-ray image that is a plurality of images in which the plurality of anatomical regions are respectively decomposed and shown;

compare the second pseudo X-ray image and the third pseudo X-ray image;

update a value of a parameter for use in generating the second pseudo X-ray image based on a result of the comparison; and repeat the input of the three-dimensional CT image, the generation of the first pseudo X-ray image, the generation of the second pseudo X-ray image, the acquisition of the label image, the generation of the masked CT image, the generation of the third pseudo X-ray image, the comparison of the second pseudo X-ray image and the third pseudo X-ray image, and the update of the value of the parameter until a predetermined condition is satisfied.

13. An image processing apparatus comprising:

a processor, wherein the processor is configured to:

acquire a simple X-ray image or a pseudo X-ray image; and convert the acquired simple X-ray image or pseudo X-ray image with a parameter updated by the learning method according to claim 1 to generate a decomposed image that is a plurality of images in which a plurality of anatomical regions of the subject are respectively decomposed and shown.

14. The image processing apparatus according to claim 13, wherein the processor is configured to convert the decomposed image into a segmentation label.

15. A non-transitory, computer-readable tangible recording medium which records thereon a learning program that causes a learning apparatus including a processor to execute the learning method according to claim 1.

16. A non-transitory, computer-readable tangible recording medium which records thereon an image processing program that causes an image processing apparatus including a processor to execute the image processing method according to claim 10.

17. The non-transitory, computer-readable tangible recording medium according to claim 16, wherein the image processing program causes the processor to further execute converting the decomposed image into a segmentation label.

\* \* \* \* \*